United States Patent
Betts et al.

(10) Patent No.: US 10,781,443 B2
(45) Date of Patent: *Sep. 22, 2020

(54) METHODS FOR ADDING ADAPTERS TO NUCLEIC ACIDS AND COMPOSITIONS FOR PRACTICING THE SAME

(71) Applicant: Takara Bio USA, Inc., Mountain View, CA (US)

(72) Inventors: Craig Betts, Mountain View, CA (US); Steve Oh, St. Louis, MO (US); George G. Jokhadze, Mountain View, CA (US); Nathalie Bolduc, Mountain View, CA (US)

(73) Assignee: Takara Bio USA, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/469,364

(22) Filed: Mar. 24, 2017

(65) Prior Publication Data
US 2017/0198285 A1  Jul. 13, 2017

Related U.S. Application Data

(63) Continuation of application No. 14/478,978, filed on Sep. 5, 2014.
(Continued)

(51) Int. Cl.
C12P 19/34 (2006.01)
C12N 15/10 (2006.01)
C12Q 1/6853 (2018.01)

(52) U.S. Cl.
CPC ..... *C12N 15/1068* (2013.01); *C12N 15/1096* (2013.01); *C12Q 1/6853* (2013.01);
(Continued)

(58) Field of Classification Search
USPC .......... 435/6.1, 6.11, 6.12, 91.1, 91.2, 91.51, 435/183; 436/94, 501; 536/23.1, 24.3,
(Continued)

(56) References Cited

U.S. PATENT DOCUMENTS 5,683,896 A  11/1997  Hartley et al.
5,962,271 A  10/1999  Chenchick et al.
(Continued)

FOREIGN PATENT DOCUMENTS

DE  19601385  7/1997
EP  1369 480  12/2003
(Continued)

OTHER PUBLICATIONS

Zhu et al., Reverse Transcriptase Template Switching: A SMART Approach for Full-Length cDNA Library Construction. BioTechniques, 30, 892-897, 2001.*
(Continued)

*Primary Examiner* — Frank W Lu
(74) *Attorney, Agent, or Firm* — Bret E. Field; Bozicevic, Field & Francis LLP

(57) ABSTRACT

Provided are methods of adding adapters to nucleic acids. The methods include combining in a reaction mixture a template ribonucleic acid (RNA), a template switch oligonucleotide including a 3' hybridization domain and a sequencing platform adapter construct, a polymerase, and dNTPs. The reaction mixture components are combined under conditions sufficient to produce a product nucleic acid that includes the template RNA and the template switch oligonucleotide each hybridized to adjacent regions of a single product nucleic acid that includes a region polymerized from the dNTPs by the polymerase. Aspects of the invention further include compositions and kits.

25 Claims, 6 Drawing Sheets

Specification includes a Sequence Listing.

Related U.S. Application Data

(60) Provisional application No. 61/979,852, filed on Apr. 15, 2014, provisional application No. 61/892,372, filed on Oct. 17, 2013.

(52) U.S. Cl.
CPC ............... *C12Y 207/07007* (2013.01); *C12Y 207/07049* (2013.01)

(58) Field of Classification Search
USPC .............................................. 536/24.33, 25.3
See application file for complete search history.

(56) References Cited

U.S. PATENT DOCUMENTS

| | | | |
|---|---|---|---|
| 5,962,272 | A | 10/1999 | Chenchik et al. |
| 6,251,639 | B1 | 6/2001 | Kurn |
| 6,287,823 | B1 | 9/2001 | Hartley |
| 6,406,890 | B1 | 6/2002 | Mueller |
| 6,518,026 | B2 | 2/2003 | Hartley |
| 7,115,400 | B1 * | 10/2006 | Adessi ................ C12Q 1/6837 435/91.2 |
| 7,435,572 | B2 | 10/2008 | Bitinaite |
| 8,124,340 | B2 | 2/2012 | Rashtchian |
| 8,440,401 | B2 | 5/2013 | Bitinaite |
| 9,410,173 | B2 | 8/2016 | Betts |
| 2004/0002090 | A1 | 1/2004 | Mayer |
| 2004/0023207 | A1 | 2/2004 | Polansky |
| 2006/0099589 | A1 | 5/2006 | Pedersen et al. |
| 2007/0212704 | A1 | 9/2007 | Dong et al. |
| 2008/0145844 | A1 | 6/2008 | Barsova et al. |
| 2008/0009420 | A1 | 7/2008 | Schroth et al. |
| 2008/0182239 | A1 | 10/2008 | Mullinax |
| 2009/0220969 | A1 | 9/2009 | Chiang |
| 2012/0010091 | A1 | 1/2012 | Linnarson et al. |
| 2012/0053063 | A1 * | 3/2012 | Rigatti ................ C12Q 1/6874 506/2 |
| 2012/0283106 | A1 | 11/2012 | Wang et al. |
| 2014/0087954 | A1 * | 3/2014 | Seligmann ........... C12Q 1/6869 506/2 |
| 2014/0242581 | A1 | 8/2014 | Johnson |
| 2015/0079600 | A1 | 3/2015 | Bergmann |
| 2015/0197787 | A1 * | 7/2015 | Welder ................ C12Q 1/6806 506/2 |

FOREIGN PATENT DOCUMENTS

| | | |
|---|---|---|
| JP | 2009-17824 A | 1/2009 |
| JP | 2009-509565 A | 3/2009 |
| JP | 2010500044 A | 1/2010 |
| JP | 2010516284 A | 5/2010 |
| JP | 2011-135822 A | 7/2011 |
| KR | 2002-0036685 | 5/2002 |
| WO | WO19972445 | 1/1996 |
| WO | WO01/09310 | 2/2001 |
| WO | WO02/00938 | 1/2002 |
| WO | WO02/068629 | 9/2002 |
| WO | WO2005/019452 | 3/2005 |
| WO | WO2012042374 | 4/2012 |
| WO | WO2012/116146 | 8/2012 |
| WO | W20130123442 | 8/2013 |
| WO | WO2014/066179 | 5/2014 |
| WO | W020150057319 | 4/2015 |
| WO | WO2015/173402 | 11/2015 |

OTHER PUBLICATIONS

Hernandez, et al. "Identification of anaplastic lymphoma kinase variant translocations using 5'RACE", Methods Mol med. 2005;115:295-314.

Hoshino, et al "A comparative study of microbial diversity and community structure in marine sediments using poly A) tailing and reverse transcription-PCR", Front Microbial. 2013; 4: 160.

Islam et al. "Highly multiplexed and strand-specific single-cell RNA 5' end sequencing", Nature Protocols 7 {2012), 813-828.

Kapteyn et al. "Incorporation of non-natural nucleotides into template-switching oligonucleotides reduces background and improves eDNA synthesis from very small RNA samples," BMC Genomics, 2010, 11: 413.

Kivioja et al. "Counting absolute numbers of molecules using unique molecular identifiers", Nature Methods 9 {2012), 72-74.

Kurzynska-Kokorniak et al. "DNA-directed DNA Polymerase and Strand Displacement Activity of the Reverse Transcriptase Encoded by the R2 Retrotransposon", Journal of Molecular Biology 374{2): 322-333 (2007).

Levin et al. "Comprehensive comparative analysis of strand-specific RNA sequencing methods", Nature Methods 7 (2010), 709-715.

Oz-Gleenberg et al. "Reverse transcriptases can clamp together nucleic acids strands with two complementary bases at their 3'-termini for initiating DNA synthesis", Nucleic Acids Research 39(3): 1042-1053 (2010).

Oz-Gleenberg et al. "Substrate variations that affect the nucleic acid clamp activity of reverse transcriptases", FEBS Journal279(10): 1894-1903 (2012).

Picelli, et al_"Full-length RNA-seq from single cells using Smart-seq2", Nature Protocols 9,171-181 (2014 ), Abstract Only.

Schramm et al. "A simple and reliable 5'-RACE approach", Nucleic Acids Research, 2000, vol. 28, No. 22, e96, 4 pages.

Shi, et al. "Poly(T) adaptor RT-PCR", Methods Mol Biol. 2012;822:53-66. doi: 10.1007/978-1-61779-427-8_4.

Turchinovich et al. "Capture and Amplification by Tailing and Switching (CATS): An ultrasensitive ligation-independent method for generation of DNA libraries for deep sequencing from pictogram amounts of DNA and RNA", RNA Biology, vol. 11, No. 7, pp. 817-828 (Jul. 2014).

Zhuang et al. "Structural bias in T4 RNA ligase-mediated 3'-adapter ligation", Nucleic Acids Research 40(7): e54 (2012), 14 pages.

Matz et al. "Amplification of eDNA ends based on template-switching effect and step-out PCR," Nucleic Acids Research, 1999, vol. 27, No. 6, 1558-1560.

TAKARA / CLONTECH, "SMART™/SMARTer™ Technology," Marketing Catalogue, Dec. 2010, pp. 1-4.

Ramskold, et al. "Full-length mRNA-Seq from single-cell levels of RNA and individual circulating tumor cells", Nature Biotechnology, vol. 30, No. 8, Jul. 22, 2012 (Jul. 22, 2012), pp. 777-782.

Ramskold, et al. Supplementary figure for XP055280564, , Jul. 22, 2012 (Jul. 22, 2012), XP055354766, Retrieved from the Internet: URL:http://www.nature.com/nbVjournal/v30/n8/extref/nbt.2282-S1.pdf, [retrieved on Mar. 14, 2017], 11 pages.

CLONTECHniques, Nn Nn: "Creator(TM) SMART(TM) Library Construction Kit", CLONETECHniques, Oct. 1, 2001 (Oct. 1, 2001 ), pp. 1-2, XP055354740, Retrieved from the Internet: URL:http://www.ebiotrade.com/emgzf/clnt/CreatorSmart.pdf [retrieved on Mar. 14, 2017], 2 pages.

Harbers, et al. "Comparison of RNA- or LNA-hybrid oligonucleotides in template-switching eactions for high-speed sequencing library preparation", BMC Genomics 2013, 14:665, 6 pages.

Tang, et al. "Suppression of artifacts and barcode bias in high-throughput transcriptome analyses utilizing template switching", Nucleic Acids Res. Feb. 1, 2013;41(3):e44, 12 pages.

Salimullah, et al. "NanoCAGE: a high-resolution technique to discover and interrogate cell transcriptomes", Cold Spring Harb Protoc. Jan. 1, 2011 ; 2011 ( 1): pp. 1-16.

Zhao et al., A Simple and Fast Method for Profiling MicroRNA Expression from Low-input Total RNA by Microarray, IUBMB Life, Jul. 2012, vol. 64, No. 7, p. 612-616.

Cloonan et al., Stem cell transcriptome profiling via massive-scale mRNA sequencing, Nature Methods, Jul. 2008, vol. 5, No. 7, p. 613-619.

\* cited by examiner

METHODS FOR ADDING ADAPTERS TO NUCLEIC ACIDS AND COMPOSITIONS FOR PRACTICING THE SAME

CROSS REFERENCE To RELATED APPLICATIONS

This application is a continuation of U.S. application Ser. No. 14/478,978 filed Sep. 5, 2014; which application, pursuant to 35 U.S.C. § 119 (e), claims priority to the filing date of the U.S. Provisional Patent Application Ser. No. 61/892,372 filed Oct. 17, 2013 and U.S. Provisional Patent Application Ser. No. 61/979,852 filed Apr. 15, 2014; the disclosures of which applications are herein incorporated by reference.

INTRODUCTION

Massively parallel (or "next generation") sequencing platforms are rapidly transforming data collection and analysis in genome, epigenome and transcriptome research. Certain sequencing platforms, such as those marketed by Illumina®, Ion Torrent™, Roche™, and Life Technologies™, involve solid phase amplification of polynucleotides of unknown sequence. Solid phase amplification of these polynucleotides is typically performed by first ligating known adapter sequences to each end of the polynucleotide. The double-stranded polynucleotide is then denatured to form a single-stranded template molecule. The adapter sequence on the 3' end of the template is hybridized to an extension primer that is immobilized on the solid substrate, and amplification is performed by extending the immobilized primer. In what is often referred to as "bridge PCR", a second immobilized primer, identical to the 5' end of the template, serves as a reverse primer, allowing amplification of both the forward and reverse strands to proceed on the solid substrate, e.g., a bead or surface of a flow cell.

A disadvantage of ligation-based approaches for sequencing adapter addition is the number of steps involved, including the enzymatic and wash steps that are needed to prepare the target polynucleotide before solid phase amplification can be initiated. As one example, after ligation of the adapter sequences, unused adapter molecules must be separated from the ligated polynucleotides before adding the mixture to the flow cell. Otherwise, the unused adapter molecules can also hybridize to the immobilized primers, preventing efficient hybridization of the primers to the template molecules and subsequent extension.

An additional drawback of ligation-based approaches is their lack of directionality, which makes it difficult to have different adapters at the different ends of the nucleic acids. Moreover, the sensitivity of such methods is low and renders them unsuitable under circumstances where only a small amount of sample material is available.

SUMMARY

Provided are methods of adding adapters to nucleic acids. The methods include combining in a reaction mixture a template ribonucleic acid (RNA), a template switch nucleic acid (e.g., a template switch oligonucleotide) including a 3' hybridization domain and a sequencing platform adapter construct, a polymerase, and dNTPs. The reaction mixture components are combined under conditions sufficient to produce a product nucleic acid that includes the template RNA and the template switch oligonucleotide each hybridized to adjacent regions of a single product nucleic acid that includes a region polymerized from the dNTPs by the polymerase. Aspects of the invention further include compositions and kits.

DETAILED DESCRIPTION

Figure 1:
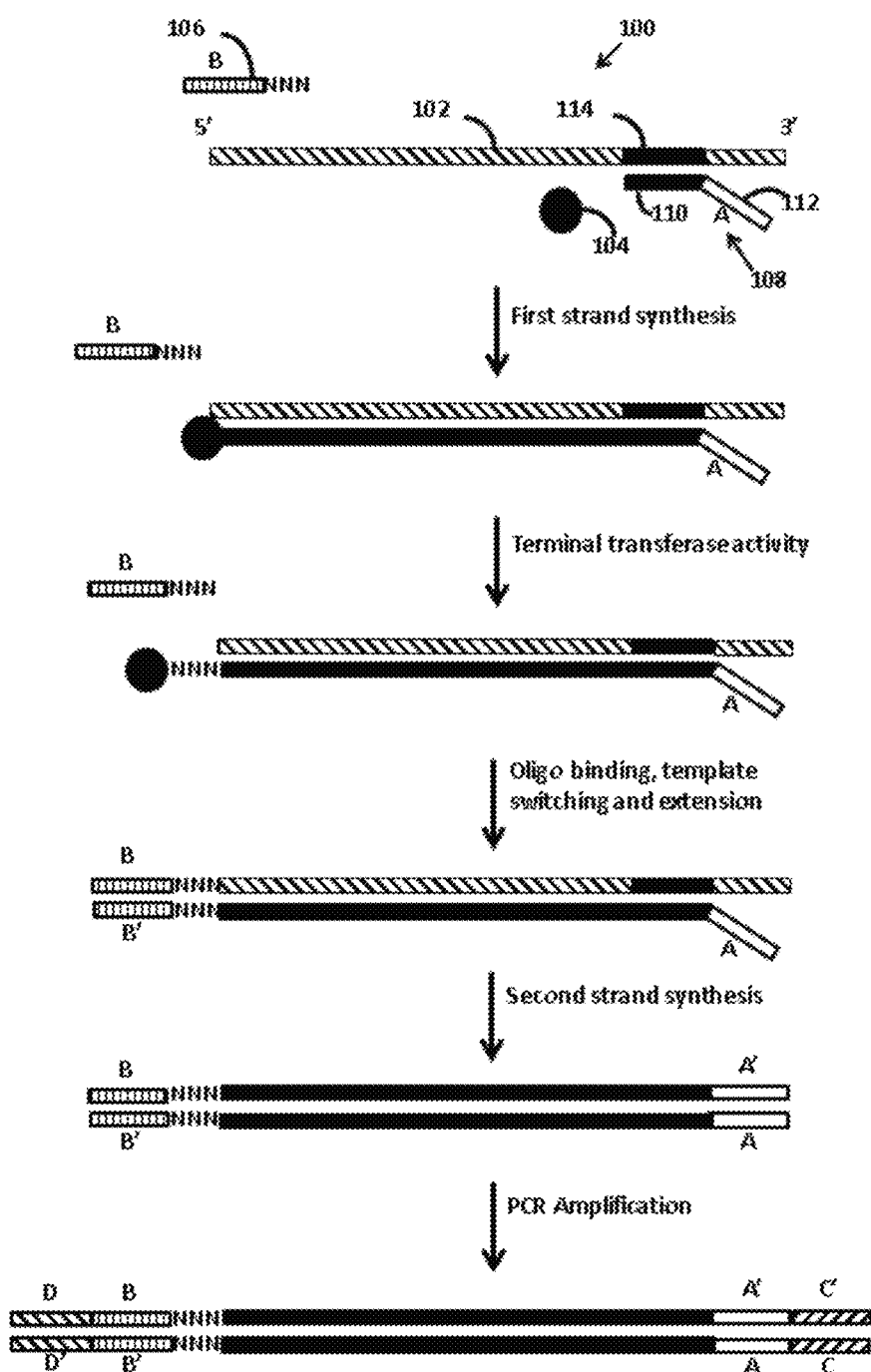
FIG. 1 schematically illustrates a template switch-based method for generating a nucleic acid having adapter constructs according to one embodiment of the present disclosure. In this embodiment, adapter constructs having less than all nucleic acid domains necessary for a sequencing platform of interest are provided by a template-switch polymerization reaction. The remaining nucleic acid domains are provided by polymerase chain reaction (PCR) using amplification primers that include the remaining domains.

Provided are methods of adding adapters to nucleic acids. The methods include combining in a reaction mixture a template ribonucleic acid (RNA), a template switch oligonucleotide including a 3' hybridization domain and a sequencing platform adapter construct, a polymerase, and dNTPs. The reaction mixture components are combined under conditions sufficient to produce a product nucleic acid that includes the template RNA and the template switch oligonucleotide each hybridized to adjacent regions of a single product nucleic acid that includes a region polymerized from the dNTPs by the polymerase. Aspects of the invention further include compositions and kits.

Before the methods of the present disclosure are described in greater detail, it is to be understood that the methods are not limited to particular embodiments described, as such may, of course, vary. It is also to be understood that the terminology used herein is for the purpose of describing particular embodiments only, and is not intended to be limiting, since the scope of the methods will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the methods. The upper and lower limits of these smaller ranges may independently be included in the smaller ranges and are also encompassed within the methods, subject to any specifically excluded limit in the stated range. Where the stated range includes one or both of the limits, ranges excluding either or both of those included limits are also included in the methods.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the methods belong. Although any methods similar or equivalent to those described herein can also be used in the practice or testing of the methods, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present methods are not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the methods, which are, for clarity, described in the context of separate embodiments, may also be provided in combination in a single embodiment. Conversely, various features of the methods, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed, to the extent that such combinations embrace operable processes and/or devices/systems/kits. In addition, all sub-combinations listed in the embodiments describing such variables are also specifically embraced by the present methods and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order which is logically possible.

METHODS

Methods of adding adapters to nucleic acids are provided. The methods utilize the ability of certain nucleic acid polymerases to "template switch," using a first ribonucleic acid (RNA) strand as a template for polymerization, and then switching to a second template nucleic acid strand (which may be referred to as a "template switch nucleic acid" or an "acceptor template") while continuing the polymerization reaction. The result is the synthesis of a hybrid nucleic acid strand with a 5' region complementary to the first template nucleic acid strand and a 3' region complementary to the template switch nucleic acid. In certain aspects, the nucleotide sequence of all or a portion (e.g., a 5' region) of the template switch oligonucleotide may be defined by a practitioner of the subject methods such that the newly-synthesized hybrid nucleic acid strand has a partial or complete sequencing platform adapter sequence at its 3' end useful for sequencing the hybrid nucleic acid strand using a sequencing platform of interest. Sequencing platforms of interest include, but are not limited to, the HiSeq™ MiSeq™ and Genome Analyzer™ sequencing systems from Illumina®; the Ion PGM™ and Ion Proton™ sequencing systems from Ion Torrent™; the PACBIO RS II sequencing system from Pacific Biosciences, the SOLiD sequencing systems from Life Technologies™, the 454 GS FLX+ and GS Junior sequencing systems from Roche, or any other sequencing platform of interest.

In certain aspects, the polymerization reaction is initiated using a primer having a partial or complete sequencing platform adapter sequence at its 5' end, resulting in a hybrid nucleic acid strand having a partial or complete sequencing platform adapter sequence at each end. The directionality of the adapters in the hybrid nucleic acid strand may be predetermined by a practitioner of the subject methods, e.g., by selecting the adapter sequence present at the 5' end of the primer, and the adapter sequence present at the 5' end of the template switch oligonucleotide. Here, the adapter sequence present in the primer and the adapter sequence in the template switch oligonucleotide will be present at the 5' and 3' ends of the hybrid nucleic acid strand, respectively.

According to the methods of the present disclosure, the reaction mixture components are combined under conditions sufficient to produce a product nucleic acid that includes the template RNA and the template switch oligonucleotide each hybridized to adjacent regions of a single product nucleic acid that includes a region polymerized from the dNTPs by the polymerase.

By "conditions sufficient to produce a product nucleic acid" is meant reaction conditions that permit polymerase-mediated extension of a 3' end of a nucleic acid strand hybridized to the template RNA, template switching of the polymerase to the template switch oligonucleotide, and continuation of the extension reaction using the template switch oligonucleotide as the template. Achieving suitable reaction conditions may include selecting reaction mixture components, concentrations thereof, and a reaction temperature to create an environment in which the polymerase is active and the relevant nucleic acids in the reaction interact (e.g., hybridize) with one another in the desired manner. For example, in addition to the template RNA, the polymerase, the template switch oligonucleotide and dNTPs, the reaction mixture may include buffer components that establish an appropriate pH, salt concentration (e.g., KCl concentration), metal cofactor concentration (e.g., $Mg^{2+}$ or $Mn^{2+}$ concentration), and the like, for the extension reaction and template switching to occur. Other components may be included, such as one or more nuclease inhibitors (e.g., an RNase inhibitor and/or a DNase inhibitor), one or more additives for facilitating amplification/replication of GC rich sequences (e.g., GC-Melt™ reagent (Clontech Laboratories, Inc. (Mountain View, Calif.)), betaine, DMSO, ethylene glycol, 1,2-propanediol, or combinations thereof), one or more molecular crowding agents (e.g., polyethylene glycol, or the like), one or more enzyme-stabilizing components (e.g., DTT present at a final concentration ranging from 1 to 10 mM (e.g., 5 mM)), and/or any other reaction mixture components useful for facilitating polymerase-mediated extension reactions and template-switching.

The reaction mixture can have a pH suitable for the primer extension reaction and template-switching. In certain embodiments, the pH of the reaction mixture ranges from 5 to 9, such as from 7 to 9, including from 8 to 9, e.g., 8 to 8.5. In some instances, the reaction mixture includes a pH adjusting agent. pH adjusting agents of interest include, but are not limited to, sodium hydroxide, hydrochloric acid, phosphoric acid buffer solution, citric acid buffer solution, and the like. For example, the pH of the reaction mixture can be adjusted to the desired range by adding an appropriate amount of the pH adjusting agent.

The temperature range suitable for production of the product nucleic acid may vary according to factors such as the particular polymerase employed, the melting temperatures of any optional primers employed, etc. According to one embodiment, the polymerase is a reverse transcriptase (e.g., an MMLV reverse transcriptase) and the reaction mixture conditions sufficient to produce the product nucleic acid include bringing the reaction mixture to a temperature ranging from 4° C. to 72° C., such as from 16° C. to 70° C., e.g., 37° C. to 50° C., such as 40° C. to 45° C., including 42° C.

The template ribonucleic acid (RNA) may be a polymer of any length composed of ribonucleotides, e.g., 10 bases or longer, 20 bases or longer, 50 bases or longer, 100 bases or longer, 500 bases or longer, 1000 bases or longer, 2000 bases or longer, 3000 bases or longer, 4000 bases or longer, 5000 bases or longer or more bases. In certain aspects, the template ribonucleic acid (RNA) is a polymer composed of ribonucleotides, e.g., 10 bases or less, 20 bases or less, 50 bases or less, 100 bases or less, 500 bases or less, 1000 bases or less, 2000 bases or less, 3000 bases or less, 4000 bases or less, or 5000 bases or less. The template RNA may be any type of RNA (or sub-type thereof) including, but not limited to, a messenger RNA (mRNA), a microRNA (miRNA), a small interfering RNA (siRNA), a transacting small interfering RNA (ta-siRNA), a natural small interfering RNA (nat-siRNA), a ribosomal RNA (rRNA), a transfer RNA (tRNA), a small nucleolar RNA (snoRNA), a small nuclear RNA (snRNA), a long non-coding RNA (lncRNA), a non-coding RNA (ncRNA), a transfer-messenger RNA (tmRNA), a precursor messenger RNA (pre-mRNA), a small Cajal body-specific RNA (scaRNA), a piwi-interacting RNA (piRNA), an endoribonuclease-prepared siRNA (esiRNA), a small temporal RNA (stRNA), a signal recognition RNA, a telomere RNA, a ribozyme, or any combination of RNA types thereof or subtypes thereof.

The RNA sample that includes the template RNA may be combined into the reaction mixture in an amount sufficient for producing the product nucleic acid. According to one embodiment, the RNA sample is combined into the reaction mixture such that the final concentration of RNA in the reaction mixture is from 1 fg/μL to 10 μg/μL, such as from 1 pg/μL to 5 μg/μL, such as from 0.001 μg/μL to 2.5 μg/μL, such as from 0.005 μg/μL to 1 μg/μL, such as from 0.01 μg/μL to 0.5 μg/μL, including from 0.1 μg/μL to 0.25 μg/μL. In certain aspects, the RNA sample that includes the template RNA is isolated from a single cell. In other aspects, the RNA sample that includes the template RNA is isolated from 2, 3, 4, 5, 6, 7, 8, 9, 10 or more, 20 or more, 50 or more, 100 or more, or 500 or more cells. According to certain embodiments, the RNA sample that includes the template RNA is isolated from 500 or less, 100 or less, 50 or less, 20 or less, 10 or less, 9, 8, 7, 6, 5, 4, 3, or 2 cells.

The template RNA may be present in any nucleic acid sample of interest, including but not limited to, a nucleic acid sample isolated from a single cell, a plurality of cells (e.g., cultured cells), a tissue, an organ, or an organism (e.g., bacteria, yeast, or the like). In certain aspects, the nucleic acid sample is isolated from a cell(s), tissue, organ, and/or the like of a mammal (e.g., a human, a rodent (e.g., a mouse), or any other mammal of interest). In other aspects, the nucleic acid sample is isolated from a source other than a mammal, such as bacteria, yeast, insects (e.g., *drosophila*), amphibians (e.g., frogs (e.g., *Xenopus*)), viruses, plants, or any other non-mammalian nucleic acid sample source.

Approaches, reagents and kits for isolating RNA from such sources are known in the art. For example, kits for isolating RNA from a source of interest—such as the NucleoSpin®, NucleoMag® and NucleoBond® RNA isolation kits by Clontech Laboratories, Inc. (Mountain View, Calif.)—are commercially available. In certain aspects, the RNA is isolated from a fixed biological sample, e.g., formalin-fixed, paraffin-embedded (FFPE) tissue. RNA from FFPE tissue may be isolated using commercially available kits—such as the NucleoSpin® FFPE RNA kits by Clontech Laboratories, Inc. (Mountain View, Calif.).

In certain aspects, the subject methods include producing the template RNA from a precursor RNA. For example, when it is desirable to control the size of the template RNA that is combined into the reaction mixture, an RNA sample isolated from a source of interest may be subjected to shearing/fragmentation, e.g., to generate a template RNA that is shorter in length as compared to a precursor non-sheared RNA (e.g., a full-length mRNA) in the original sample. The template RNA may be generated by a shearing/fragmentation strategy including, but not limited to, passing the sample one or more times through a micropipette tip or fine-gauge needle, nebulizing the sample, sonicating the sample (e.g., using a focused-ultrasonicator by Covaris, Inc. (Woburn, Mass.)), bead-mediated shearing, enzymatic shearing (e.g., using one or more RNA-shearing enzymes), chemical based fragmentation, e.g., using divalent cations, fragmentation buffer (which may be used in combination with heat) or any other suitable approach for shearing/fragmenting a precursor RNA to generate a shorter template RNA. In certain aspects, the template RNA generated by shearing/fragmentation of a starting nucleic acid sample has a length of from 10 to 20 nucleotides, from 20 to 30 nucleotides, from 30 to 40 nucleotides, from 40 to 50 nucleotides, from 50 to 60 nucleotides, from 60 to 70 nucleotides, from 70 to 80 nucleotides, from 80 to 90 nucleotides, from 90 to 100 nucleotides, from 100 to 150 nucleotides, from 150 to 200, from 200 to 250 nucleotides in length, or from 200 to 1000 nucleotides or even from 1000 to 10,000 nucleotides, for example, as appropriate for the sequencing platform chosen.

Additional strategies for producing the template RNA from a precursor RNA may be employed. For example, producing the template RNA may include adding nucleotides to an end of the precursor RNA. In certain aspects, the precursor RNA is a non-polyadenylated RNA (e.g., a microRNA, small RNA, or the like), and producing the template RNA includes adenylating (e.g., polyadenylating) the precursor RNA.

Adenylating the precursor RNA may be performed using any convenient approach. According to certain embodiments, the adenylation is performed enzymatically, e.g., using Poly(A) polymerase or any other enzyme suitable for catalyzing the incorporation of adenine residues at the 3' terminus of the precursor RNA. Reaction mixtures for carrying out the adenylation reaction may include any useful components, including but not limited to, a polymerase, a buffer (e.g., a Tris-HCL buffer), one or more metal cations (e.g., $MgCl_2$, $MnCl_2$, or combinations thereof), a salt (e.g., NaCl), one or more enzyme-stabilizing components (e.g., DTT), ATP, and any other reaction components useful for facilitating the adenylation of a precursor RNA. The adenylation reaction may be carried out at a temperature (e.g., 30° C.-50° C., such as 37° C.) and pH (e.g., pH 7-pH 8.5, such as pH 7.9) compatible with the polymerase being employed, e.g., polyA polymerase. Other approaches for adding nucleotides to a precursor RNA include ligation-based strategies, where an RNA ligase (e.g., T4 RNA ligase) catalyzes the covalent joining of a defined sequence to an end (e.g., the 3' end) of the precursor RNA to produce the template RNA.

The methods of the present disclosure include combining a polymerase into the reaction mixture. A variety of polymerases may be employed when practicing the subject methods. The polymerase combined into the reaction mixture is capable of template switching, where the polymerase uses a first nucleic acid strand as a template for polymerization, and then switches to the 3' end of a second "acceptor" template nucleic acid strand to continue the same polymerization reaction. In certain aspects, the polymerase combined into the reaction mixture is a reverse transcriptase (RT). Reverse transcriptases capable of template-switching that find use in practicing the methods include, but are not limited to, retroviral reverse transcriptase, retrotransposon reverse transcriptase, retroplasmid reverse transcriptases, retron reverse transcriptases, bacterial reverse transcriptases, group II intron-derived reverse transcriptase, and mutants, variants derivatives, or functional fragments thereof. For example, the reverse transcriptase may be a Moloney Murine Leukemia Virus reverse transcriptase (MMLV RT) or a *Bombyx mori* reverse transcriptase (e.g., *Bombyx mori* R2 non-LTR element reverse transcriptase). Polymerases capable of template switching that find use in practicing the subject methods are commercially available and include SMARTScribe™ reverse transcriptase available from Clontech Laboratories, Inc. (Mountain View, Calif.). In certain aspects, a mix of two or more different polymerases is added to the reaction mixture, e.g., for improved processivity, proof-reading, and/or the like. In some instances, the polymer is one that is heterologous relative to the template, or source thereof.

The polymerase is combined into the reaction mixture such that the final concentration of the polymerase is sufficient to produce a desired amount of the product nucleic acid. In certain aspects, the polymerase (e.g., a reverse transcriptase such as an MMLV RT or a *Bombyx mori* RT) is present in the reaction mixture at a final concentration of from 0.1 to 200 units/µL (U/µL), such as from 0.5 to 100 U/µL, such as from 1 to 50 U/µL, including from 5 to 25 U/µL, e.g., 20 U/µL.

In addition to a template switching capability, the polymerase combined into the reaction mixture may include other useful functionalities to facilitate production of the product nucleic acid. For example, the polymerase may have terminal transferase activity, where the polymerase is capable of catalyzing template-independent addition of deoxyribonucleotides to the 3' hydroxyl terminus of a DNA molecule. In certain aspects, when the polymerase reaches the 5' end of the template RNA, the polymerase is capable of incorporating one or more additional nucleotides at the 3' end of the nascent strand not encoded by the template. For example, when the polymerase has terminal transferase activity, the polymerase may be capable of incorporating 1, 2, 3, 4, 5, 6, 7, 8, 9, 10 or more additional nucleotides at the 3' end of the nascent DNA strand. In certain aspects, a polymerase having terminal transferase activity incorporates 10 or less, such as 5 or less (e.g., 3) additional nucleotides at the 3' end of the nascent DNA strand. All of the nucleotides may be the same (e.g., creating a homonucleotide stretch at the 3' end of the nascent strand) or at least one of the nucleotides may be different from the other(s). In certain aspects, the terminal transferase activity of the polymerase results in the addition of a homonucleotide stretch of 2, 3, 4, 5, 6, 7, 8, 9, 10 or more of the same nucleotides (e.g., all dCTP, all dGTP, all dATP, or all dTTP). According to certain embodiments, the terminal transferase activity of the polymerase results in the addition of a homonucleotide stretch of 10 or less, such as 9, 8, 7, 6, 5, 4, 3, or 2 (e.g., 3) of the same nucleotides. For example, according to one embodiment, the polymerase is an MMLV reverse transcriptase (MMLV RT). MMLV RT incorporates additional nucleotides (predominantly dCTP, e.g., three dCTPs) at the 3' end of the nascent DNA strand. As described in greater detail elsewhere herein, these additional nucleotides may be useful for enabling hybridization between the 3' end of the template switch oligonucleotide and the 3' end of the nascent DNA strand, e.g., to facilitate template switching by the polymerase from the template RNA to the template switch oligonucleotide.

As set forth above, the subject methods include combining a template switch nucleic acid into the reaction mixture. In certain aspects, the template switch nucleic acid is a template switch oligonucleotide. By "template switch oligonucleotide" is meant an oligonucleotide template to which a polymerase switches from an initial template (e.g., the template RNA in the subject methods) during a nucleic acid polymerization reaction. In this regard, the template RNA may be referred to as a "donor template" and the template switch oligonucleotide may be referred to as an "acceptor template." As used herein, an "oligonucleotide" is a single-stranded multimer of nucleotides from 2 to 500 nucleotides, e.g., 2 to 200 nucleotides. Oligonucleotides may be synthetic or may be made enzymatically, and, in some embodiments, are 10 to 50 nucleotides in length. Oligonucleotides may contain ribonucleotide monomers (i.e., may be oligoribonucleotides or "RNA oligonucleotides") or deoxyribonucleotide monomers (i.e., may be oligodeoxyribonucleotides or "DNA oligonucleotides"). Oligonucleotides may be 10 to 20, 21 to 30, 31 to 40, 41 to 50, 51 to 60, 61 to 70, 71 to 80, 80 to 100, 100 to 150 or 150 to 200, up to 500 or more nucleotides in length, for example.

The reaction mixture includes the template switch oligonucleotide at a concentration sufficient to permit template switching of the polymerase from the template RNA to the template switch oligonucleotide. For example, the template switch oligonucleotide may be added to the reaction mixture at a final concentration of from 0.01 to 100 µM, such as from 0.1 to 10 µM, such as from 0.5 to 5 µM, including 1 to 2 µM (e.g., 1.2 µM).

The template switch oligonucleotide may include one or more nucleotides (or analogs thereof) that are modified or otherwise non-naturally occurring. For example, the template switch oligonucleotide may include one or more nucleotide analogs (e.g., LNA, FANA, 2'-O-Me RNA, 2'-fluoro RNA, or the like), linkage modifications (e.g., phosphorothioates, 3'-3' and 5'-5' reversed linkages), 5' and/or 3' end modifications (e.g., 5' and/or 3' amino, biotin, DIG, phosphate, thiol, dyes, quenchers, etc.), one or more fluorescently labeled nucleotides, or any other feature that provides a desired functionality to the template switch oligonucleotide.

The template switch oligonucleotide includes a 3' hybridization domain and a sequencing platform adapter construct. The 3' hybridization domain may vary in length, and in some instances ranges from 2 to 10 nts in length, such as 3 to 7 nts in length. The sequence of the 3' hybridization may be any convenient sequence, e.g., an arbitrary sequence, a heteropolymeric sequence (e.g., a hetero-trinucleotide) or homopolymeric sequence (e.g., a homo-trinucleotide, such as G-G-G), or the like. Examples of 3' hybridization domains and template switch oligonucleotides are further described in U.S. Pat. No. 5,962,272, the disclosure of which is herein incorporated by reference. In addition to a 3' hybridization domain, the template switch oligonucleotide includes a sequencing platform adapter construct. By "sequencing platform adapter construct" is meant a nucleic acid construct that includes at least a portion of a nucleic acid domain (e.g., a sequencing platform adapter nucleic acid sequence) utilized by a sequencing platform of interest, such as a sequencing platform provided by Illumina® (e.g., the HiSeq™, MiSeq™ and/or Genome Analyzer™ sequencing systems); Ion Torrent™ (e.g., the Ion PGM™ and/or Ion Proton™ sequencing systems); Pacific Biosciences (e.g., the PACBIO RS II sequencing system); Life Technologies™ (e.g., a SOLiD sequencing system); Roche (e.g., the 454 GS FLX+ and/or GS Junior sequencing systems); or any other sequencing platform of interest.

In certain aspects, the sequencing platform adapter construct includes a nucleic acid domain selected from: a domain (e.g., a "capture site" or "capture sequence") that specifically binds to a surface-attached sequencing platform oligonucleotide (e.g., the P5 or P7 oligonucleotides attached to the surface of a flow cell in an Illumina® sequencing system); a sequencing primer binding domain (e.g., a domain to which the Read 1 or Read 2 primers of the Illumina® platform may bind); a barcode domain (e.g., a domain that uniquely identifies the sample source of the nucleic acid being sequenced to enable sample multiplexing by marking every molecule from a given sample with a specific barcode or "tag"); a barcode sequencing primer binding domain (a domain to which a primer used for sequencing a barcode binds); a molecular identification domain (e.g., a molecular index tag, such as a randomized tag of 4, 6, or other number of nucleotides) for uniquely marking molecules of interest to determine expression levels based on the number of instances a unique tag is sequenced; or any combination of such domains. In certain aspects, a barcode domain (e.g., sample index tag) and a molecular identification domain (e.g., a molecular index tag) may be included in the same nucleic acid.

The sequencing platform adapter constructs may include nucleic acid domains (e.g., "sequencing adapters") of any length and sequence suitable for the sequencing platform of interest. In certain aspects, the nucleic acid domains are from 4 to 200 nucleotides in length. For example, the nucleic acid domains may be from 4 to 100 nucleotides in length, such as from 6 to 75, from 8 to 50, or from 10 to 40 nucleotides in length. According to certain embodiments, the sequencing platform adapter construct includes a nucleic acid domain that is from 2 to 8 nucleotides in length, such as from 9 to 15, from 16-22, from 23-29, or from 30-36 nucleotides in length.

The nucleic acid domains may have a length and sequence that enables a polynucleotide (e.g., an oligonucleotide) employed by the sequencing platform of interest to specifically bind to the nucleic acid domain, e.g., for solid phase amplification and/or sequencing by synthesis of the cDNA insert flanked by the nucleic acid domains. Example nucleic acid domains include the P5 (5'-AATGATACGGCGAC-CACCGA-3') (SEQ ID NO:01), P7 (5'-CAAGCA-GAAGACGGCATACGAGAT-3') (SEQ ID NO:02), Read 1 primer (5'-ACACTCTTTCCCTACACGACGCTCTTC-CGATCT-3') (SEQ ID NO:03) and Read 2 primer (5'-GTGACTGGAGTTCAGACGTGTGCTCTTCCGATCT-3') (SEQ ID NO:04) domains employed on the Illumina®-based sequencing platforms. Other example nucleic acid domains include the A adapter (5'-CCATCTCATCCCT-GCGTGTCTCCGACTCAG-3') (SEQ ID NO:05) and P1 adapter (5'-CCTCTCTATGGGCAGTCGGTGAT-3') (SEQ ID NO:06) domains employed on the Ion Torrent™-based sequencing platforms.

The nucleotide sequences of nucleic acid domains useful for sequencing on a sequencing platform of interest may vary and/or change over time. Adapter sequences are typically provided by the manufacturer of the sequencing platform (e.g., in technical documents provided with the sequencing system and/or available on the manufacturer's website). Based on such information, the sequence of the sequencing platform adapter construct of the template switch oligonucleotide (and optionally, a first strand synthesis primer, amplification primers, and/or the like) may be designed to include all or a portion of one or more nucleic acid domains in a configuration that enables sequencing the nucleic acid insert (corresponding to the template RNA) on the platform of interest.

According to certain embodiments, the template switch oligonucleotide includes a modification that prevents the polymerase from switching from the template switch oligonucleotide to a different template nucleic acid after synthesizing the compliment of the 5' end of the template switch oligonucleotide (e.g., a 5' adapter sequence of the template switch oligonucleotide). Useful modifications include, but are not limited to, an abasic lesion (e.g., a tetrahydrofuran derivative), a nucleotide adduct, an iso-nucleotide base (e.g., isocytosine, isoguanine, and/or the like), and any combination thereof.

The template switch oligonucleotide may include a sequence (e.g., a defined nucleotide sequence 5' of the 3' hybridization domain of the template switch oligonucleotide), that enables second strand synthesis and/or PCR amplification of the single product nucleic acid. For example, the template switch oligonucleotide may include a sequence, where subsequent to generating the single product nucleic acid, second strand synthesis is performed using a primer that has that sequence. The second strand synthesis produces a second strand DNA complementary to the single product nucleic acid. Alternatively, or additionally, the single product nucleic acid may be amplified using a primer pair in which one of the primers has that sequence. Accordingly, in certain aspects, the methods of the present disclosure may further include producing the product nucleic acid and contacting a 3' region of the single product nucleic acid complementary to the template switch oligonucleotide with a second strand primer configured to bind thereto under hybridization conditions. Following contacting the 3' region of the single product nucleic acid complementary to the template switch oligonucleotide with the second strand primer, the methods may further include subjecting the reaction mixture to nucleic acid polymerization conditions.

The term "complementary" as used herein refers to a nucleotide sequence that base-pairs by non-covalent bonds to all or a region of a target nucleic acid (e.g., a region of the product nucleic acid). In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. In RNA, A is complementary to U and vice versa. Typically, "complementary" refers to a nucleotide sequence that is at least partially complementary. The term "complementary" may also encompass duplexes that are fully complementary such that every nucleotide in one strand is complementary to every nucleotide in the other strand in corresponding positions. In certain cases, a nucleotide sequence may be partially complementary to a target, in which not all nucleotides are complementary to every nucleotide in the target nucleic acid in all the corresponding positions. For example, a primer may be perfectly (i.e., 100%) complementary to the target nucleic acid, or the primer and the target nucleic acid may share some degree of complementarity which is less than perfect (e.g., 70%, 75%, 85%, 90%, 95%, 99%). The percent identity of two nucleotide sequences can be determined by aligning the sequences for optimal comparison purposes (e.g., gaps can be introduced in the sequence of a first sequence for optimal alignment). The nucleotides at corresponding positions are then compared, and the percent identity between the two sequences is a function of the number of identical positions shared by the sequences (i.e., % identity=# of identical positions/total # of positions×100). When a position in one sequence is occupied by the same nucleotide as the corresponding position in the other sequence, then the molecules are identical at that position. A non-limiting example of such a mathematical algorithm is described in Karlin et al., Proc. Natl. Acad. Sci. USA 90:5873-5877 (1993). Such an algorithm is incorporated into the NBLAST and XBLAST programs (version 2.0) as described in Altschul et al., Nucleic Acids Res. 25:389-3402 (1997). When utilizing BLAST and Gapped BLAST programs, the default parameters of the respective programs (e.g., NBLAST) can be used. In one aspect, parameters for sequence comparison can be set at score=100, wordlength=12, or can be varied (e.g., wordlength=5 or wordlength=20).

As used herein, the term "hybridization conditions" means conditions in which a primer specifically hybridizes to a region of the target nucleic acid (e.g., the template RNA, the single product nucleic acid, etc.). Whether a primer specifically hybridizes to a target nucleic acid is determined by such factors as the degree of complementarity between the polymer and the target nucleic acid and the temperature at which the hybridization occurs, which may be informed by the melting temperature ($T_M$) of the primer. The melting temperature refers to the temperature at which half of the primer-target nucleic acid duplexes remain hybridized and half of the duplexes dissociate into single strands. The $T_m$ of a duplex may be experimentally determined or predicted using the following formula $T_m=81.5+16.6(\log_{10}[Na^+])+0.41$ (fraction G+C)−(60/N), where N is the chain length and [$Na^+$] is less than 1 M. See Sambrook and Russell (2001; Molecular Cloning: A Laboratory Manual, $3^{rd}$ ed., Cold Spring Harbor Press, Cold Spring Harbor N.Y., Ch. 10). Other more advanced models that depend on various parameters may also be used to predict $T_m$ of primer/target duplexes depending on various hybridization conditions. Approaches for achieving specific nucleic acid hybridization may be found in, e.g., Tijssen, Laboratory Techniques in Biochemistry and Molecular Biology-Hybridization with Nucleic Acid Probes, part I, chapter 2, "Overview of principles of hybridization and the strategy of nucleic acid probe assays," Elsevier (1993).

As described above, the subject methods include combining dNTPs into the reaction mixture. In certain aspects, each of the four naturally-occurring dNTPs (dATP, dGTP, dCTP and dTTP) are added to the reaction mixture. For example, dATP, dGTP, dCTP and dTTP may be added to the reaction mixture such that the final concentration of each dNTP is from 0.01 to 100 mM, such as from 0.1 to 10 mM, including 0.5 to 5 mM (e.g., 1 mM). According to one embodiment, at least one type of nucleotide added to the reaction mixture is a non-naturally occurring nucleotide, e.g., a modified nucleotide having a binding or other moiety (e.g., a fluorescent moiety) attached thereto, a nucleotide analog, or any other type of non-naturally occurring nucleotide that finds use in the subject methods or a downstream application of interest.

The addition of a primer to the reaction mixture is not necessary when the template RNA provides a suitable substrate for initiation of first-strand synthesis. For example, when the template RNA has double-stranded regions and an overhang at one or both of its ends, the "non-overhanging" strand of the dsRNA can prime a first-strand synthesis reaction in which the overhanging strand serves as the template. In this manner, the polymerase may be used to "fill in" the overhang, switch to the template switch oligonucleotide, and complete the first strand synthesis using the template switch oligonucleotide as an acceptor template to produce the product nucleic acid (where a terminal transferase reaction by the polymerase optionally precedes the template switch as described elsewhere herein). Accordingly, the addition of a primer is obviated when the template RNA includes, e.g., an overhang at one or both of its ends.

In certain circumstances, however, it may be desirable to add a primer to the reaction mixture to prime the synthesis of the single product nucleic acid. For example, if the template RNA is single-stranded, a primer may be useful for purposes of initiating first-strand synthesis. In addition, use of a primer can give a practitioner of the subject methods more control over which RNA(s) in an RNA sample will serve as the template RNA(s) for production of the product nucleic acid, e.g., where it is desirable to produce product nucleic acids corresponding to a template RNA of interest (e.g., polyadenylated RNA, for which an oligo dT-based primer that hybridizes to the polyA tail of the RNA may be used to prime the first strand synthesis).

Accordingly, in certain aspects, the subject methods further include contacting the template RNA with a first primer that primes the synthesis of the single product nucleic acid. The contacting is performed under conditions sufficient for the primer to hybridize to the template RNA, which conditions are described elsewhere herein. According to one embodiment, the entire sequence of the primer is arbitrary, e.g., the primer may be a random hexamer or any other random primer of suitable length (or mixtures thereof). In other aspects, the primer has a defined sequence, e.g., the primer sequence may be designed by one practicing the subject methods to specifically hybridize to a known complementary sequence in a template RNA of interest (e.g., a polyA tail of the template RNA).

According to certain embodiments, the primer includes two or more domains. For example, the primer may include a first (e.g., 3') domain that hybridizes to the template RNA and a second (e.g., 5') domain that does not hybridize to the template RNA. The sequence of the first and second domains may be independently defined or arbitrary. In certain aspects, the first domain has a defined sequence and the sequence of the second domain is defined or arbitrary. In other aspects, the first domain has an arbitrary sequence (e.g., a random sequence, such as a random hexamer sequence) and the sequence of the second domain is defined or arbitrary. According to one embodiment, the second domain includes a nucleotide sequence that is the same as, or different from, a nucleotide sequence present in the template switch oligonucleotide.

In some embodiments, the second domain of the primer includes a sequencing platform adapter construct. The sequencing platform adapter construct of the second domain may include a nucleic acid domain selected from a domain (e.g., a "capture site" or "capture sequence") that specifically binds to a surface-attached sequencing platform oligonucleotide (e.g., the P5 or P7 oligonucleotides attached to the surface of a flow cell in an Illumina® sequencing system), a sequencing primer binding domain (e.g., a domain to which the Read 1 or Read 2 primers of the Illumina® platform may bind), a barcode domain (e.g., a domain that uniquely identifies the sample source of the nucleic acid being sequenced to enable sample multiplexing by marking every molecule from a given sample with a specific barcode or "tag"), a barcode sequencing primer binding domain (a domain to which a primer used for sequencing a barcode binds), a molecular identification domain, or any combination of such domains.

In certain aspects, the sequencing platform adapter construct of the second domain of the primer is different from the sequencing platform adapter construct of the template switch oligonucleotide. Such embodiments find use, e.g., where one wishes to produce a single product nucleic acid (e.g., a cDNA or library thereof) with one end having one or more sequencing platform adapter sequences and the second end having one or more sequencing platform adapter sequences different from the first end. Having ends with different adapter sequences is useful, e.g., for subsequent solid phase amplification (e.g., cluster generation using the surface-attached P5 and P7 primers in an Illumina®-based sequencing system), DNA sequencing (e.g., using the Read 1 and Read 2 primers in an Illumina®-based sequencing system), and any other steps performed by a sequencing platform requiring different adapter sequences at opposing ends of the nucleic acid to be sequenced. Having different ends is also useful in providing strand specific information, since the directionality of the sequenced strand is defined by the different ends. Current methods in the art for doing this require multiple steps and degradation of the undesired strand—e.g., using UDG and incorporation of dU into the undesired strand. The current method is far more streamlined and requires less steps, generating strand-specific information directly.

When the methods include contacting the template RNA with a primer that primes the synthesis of the single product nucleic acid, the primer may include one or more nucleotides (or analogs thereof) that are modified or otherwise non-naturally occurring. For example, the primer may include one or more nucleotide analogs (e.g., LNA, FANA, 2'-O-Me RNA, 2'-fluoro RNA, or the like), linkage modifications (e.g., phosphorothioates, 3'-3' and 5'-5' reversed linkages), 5' and/or 3' end modifications (e.g., 5' and/or 3' amino, biotin, DIG, phosphate, thiol, dyes, quenchers, etc.), one or more fluorescently labeled nucleotides, or any other feature that provides a desired functionality to the primer that primes the synthesis of the single product nucleic acid.

In certain aspects, when the methods include contacting the template RNA with a primer that primes the synthesis of the single product nucleic acid, it may be desirable to prevent any subsequent extension reactions which use the single product nucleic acid as a template from extending beyond a particular position in the region of the single product nucleic acid corresponding to the primer. For example, according to certain embodiments, the primer that primes the synthesis of the single product nucleic acid includes a modification that prevents a polymerase using the region corresponding to the primer as a template from polymerizing a nascent strand beyond the modification. Useful modifications include, but are not limited to, an abasic lesion (e.g., a tetrahydrofuran derivative), a nucleotide adduct, an iso-nucleotide base (e.g., isocytosine, isoguanine, and/or the like), and any combination thereof.

Any nucleic acids that find use in practicing the methods of the present disclosure (e.g., the template switch oligonucleotide, a primer that primes the synthesis of the single product nucleic acid, a second strand synthesis primer, one or more primers for amplifying the product nucleic acid, and/or the like) may include any useful nucleotide analogues and/or modifications, including any of the nucleotide analogues and/or modifications described herein.

Once the product nucleic acid is produced, the methods may include inputting the product nucleic acid directly into a downstream application of interest (e.g., a sequencing application, etc.). In other aspects, the methods may include using the product nucleic acid as a template for second-strand synthesis and/or PCR amplification (e.g., for subsequent sequencing of the amplicons). According to one embodiment, the methods of the present disclosure further include subjecting the product nucleic acid to nucleic acid amplification conditions. Such conditions may include the addition of forward and reverse primers configured to amplify all or a desired portion of the product nucleic acid, dNTPs, and a polymerase suitable for effecting the amplification (e.g., a thermostable polymerase). The single product nucleic acid may have an amplification sequence at its 5' end and an amplification sequence at its 3' end, and be subjected to PCR amplification conditions with primers complementary to the 5' and 3' amplification sequences. The amplification sequences may be (or overlap with) a nucleic acid domain in a sequencing platform adapter construct, or may be outside of the sequencing platform adapter construct. An initial step in carrying out the amplification may include denaturing the product nucleic acid to dissociate the template RNA and template switch oligonucleotide from the single product nucleic acid, thereby making the single product nucleic acid available for primer binding.

In certain aspects, when the single product nucleic acid is amplified following its production, the amplification may be carried out using a primer pair in which one or both of the primers include a sequencing platform adapter construct. The sequencing platform adapter construct(s) may include any of the nucleic acid domains described elsewhere herein (e.g., a domain that specifically binds to a surface-attached sequencing platform oligonucleotide, a sequencing primer binding domain, a barcode domain, a barcode sequencing primer binding domain, a molecular identification domain, or any combination thereof). Such embodiments finds use, e.g., where the single product nucleic does not include all of the adapter domains useful or necessary for sequencing in a sequencing platform of interest, and the remaining adapter domains are provided by the primers used for the amplification of the single product nucleic acid. An example method according to this embodiment is shown in FIG. 1. As shown, template RNA 102, polymerase 104, template switch oligonucleotide 106, and dNTPs (not shown) are combined into reaction mixture 100 under conditions sufficient to produce the product nucleic acid. Template switch oligonucleotide 106 includes sequencing platform adapter construct B. Although optional, the embodiment shown in FIG. 1 employs a first primer, primer 108, which is extended by the polymerase for first strand synthesis. Primer 108 includes first (3') domain 110 that hybridizes to the template RNA and second (5') domain 112 that does not hybridize to the template RNA. The second domain includes sequencing platform adapter construct A. The nucleotide sequence of first domain 110 may be arbitrary (e.g., a random sequence, such as a random hexamer sequence) or the sequence of the first domain may be defined (e.g., a sequence specifically selected to hybridize to a particular region of a particular template RNA of interest). In this example, first domain 110 of primer 108 is complementary to sequence 114 within template RNA 102, and second domain 112 includes sequencing platform adapter construct A having one or more sequencing platform nucleic acid domains (e.g., a domain that specifically binds to a surface-attached sequencing platform oligonucleotide, a sequencing primer binding domain, a barcode domain, a barcode sequencing primer binding domain, a molecular identification domain, and combinations thereof).

Upon hybridization of primer 108 to template RNA 102, first strand synthesis proceeds when polymerase 104 extends primer 108 along template RNA 102. In this example, the polymerase has terminal transferase activity, such that when the extension reaction reaches the 5' end of the template RNA, the polymerase adds an arbitrary sequence that can be homodimeric or heterodimeric, and may range in length of nucleotides (e.g., 2 to 10 nts, such as 2 to 5 nts) such as a homonucleotide stretch (e.g., a homo-trinucleotide shown here as NNN) to the extension product. According to this embodiment, template switch oligonucleotide has a 3' hybridization domain that includes a homonucleotide stretch (shown here as a homo-trinucleotide stretch, NNN) complementary to the homonucleotide stretch at the 3' end of the extension product. This complementarity promotes hybridization of the 3' hybridization domain of the template switch oligonucleotide to the 3' end of the extension product. Hybridization brings the acceptor template region of the template switch oligonucleotide (located 5' of the 3' hybridization domain) within sufficient proximity of the polymerase such that the polymerase can template switch to the acceptor template region and continue the extension reaction to the 5' terminal nucleotide of the template switch oligonucleotide, thereby producing the product nucleic acid that includes the template RNA and the template switch oligonucleotide each hybridized to adjacent regions of the single product nucleic acid.

In this example, the template switch oligonucleotide includes sequencing platform adapter construct B having one or more sequencing platform nucleic acid domains (e.g., a domain that specifically binds to a surface-attached sequencing platform oligonucleotide, a sequencing primer binding domain, a barcode domain, a barcode sequencing primer binding domain, a molecular identification domain, and combinations thereof), such that the single product nucleic acid includes sequencing platform adapter construct A at its 5' end and sequencing platform adapter construct B' at its 3' end. According to this embodiment, the method further includes a second strand synthesis step, where a primer complementary to a 3' region of the single product nucleic acid hybridizes to the 3' region of the single product nucleic acid and is extended by a polymerase—using the single product nucleic acid as a template—to the 5' end of the single product nucleic acid. The result of this second strand synthesis step is a double-stranded DNA that includes the single product nucleic acid and its complementary strand. In the example shown in FIG. 1, adapter constructs A/A' and B/B' do not include all of the sequencing platform nucleic acid domains useful or necessary for downstream sequencing of the nucleic acid. To add the remaining sequencing platform nucleic acid domains, the nucleic acid is amplified using primers having adapter constructs C and D (e.g., present in a non-hybridizing 5' region of the primers) which provide the remaining sequencing platform nucleic acid domains. The amplicons include adapter constructs A/A' and C/C' at one end and adapter constructs B/B' and D/D' at the opposite end. One practicing the subject methods may select the sequences of the sequencing platform adapter construct of the first strand synthesis primer, the template switch oligonucleotide, and the amplification primers, to provide all of the necessary domains in a suitable configuration for sequencing on a sequencing platform of interest. As just one example, constructs A/A' and B/B' may include sequencing primer binding domains (e.g., primer binding domains for the Read 1 and Read 2 sequencing primers employed in Illumina®-based sequencing platforms), while constructs C/C' and D/D' include a domain that specifically binds to a surface-attached sequencing platform oligonucleotide (e.g., domains that specifically bind to the surface-attached P5 and P7 primers of an Illumina® sequencing system). Any of adapter constructs A/A'-D/D' may include any additional sequence elements useful or necessary for sequencing on a sequencing platform of interest.

Figure 2:
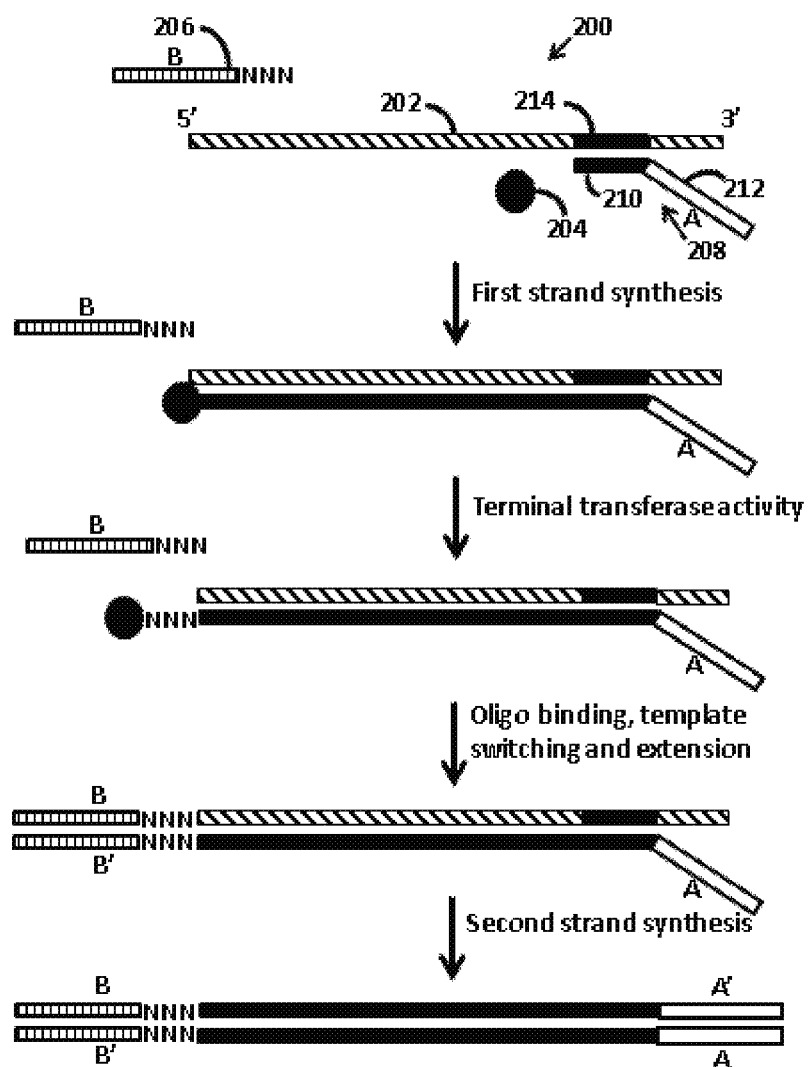
FIG. 2 schematically illustrates a template switch-based method for generating a nucleic acid having adapter constructs according to one embodiment of the present disclosure. In this embodiment, adapters that include all nucleic acid domains necessary for a sequencing platform of interest are provided during a template-switch polymerization reaction.

As summarize above, a primer having a sequencing platform adapter construct may be used to prime the synthesis of the single product nucleic acid, so that the single product nucleic acid has a sequencing platform adapter construct at its 5' and 3' ends. In certain aspects, the sequencing platform adapter constructs of the single product nucleic acid include all of the useful or necessary domains for sequencing the nucleic acid on a sequencing platform of interest. As shown in FIG. 2, a product nucleic acid is produced using an approach similar to that shown in FIG. 1. However, in the embodiment shown in FIG. 2, sequencing adapter constructs A/A' and B/B' include all of the sequencing platform nucleic acid domains useful or necessary for sequencing the single product nucleic acid on a sequencing platform of interest (e.g., a domain that specifically binds to a surface-attached sequencing platform oligonucleotide, a sequencing primer binding domain, a barcode domain, a barcode sequencing primer binding domain, a molecular identification domain, and combinations thereof). According to certain embodiments, the single product nucleic acid is PCR amplified prior to sequencing on the sequencing platform. In other embodiments, the single product nucleic acid is not amplified prior to sequencing.

Figure 3:
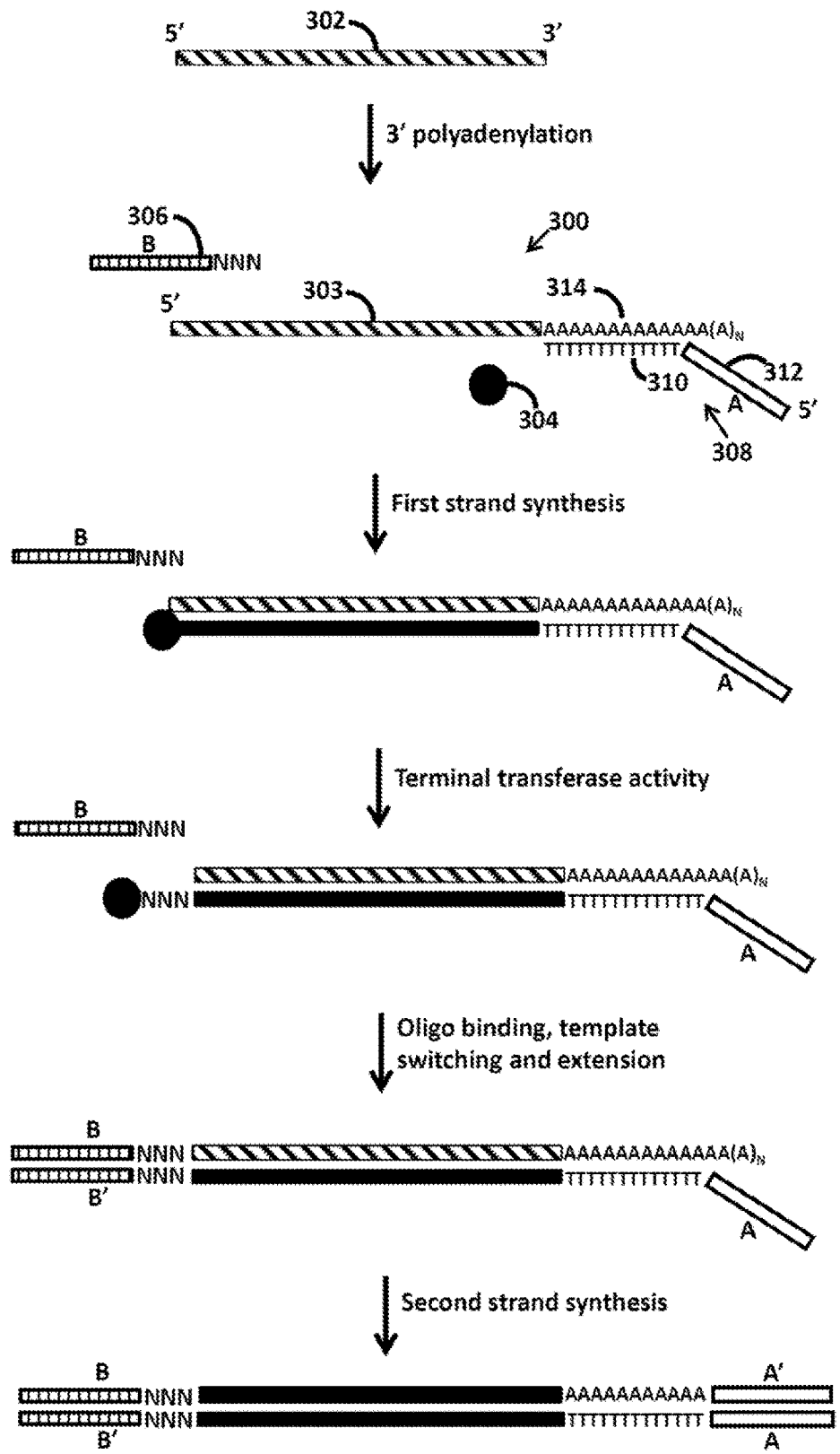
FIG. 3 schematically illustrates a template switch-based method for generating a nucleic acid having adapter constructs according to one embodiment of the present disclosure. In this embodiment, non-polyadenylated RNA is used as the starting material. The non-polyadenylated RNA is adenylated, and the adenylated RNA serves as the donor template in a template-switch polymerization reaction that generates a nucleic acid having adapter constructs. From top to bottom, SEQ ID NOs:11:12.

A method according to an additional embodiment of the present disclosure is shown in FIG. 3. In this example, non-polyadenylated precursor RNA 302 undergoes 3' polyadenylation to produce template RNA 303. In this example, first strand synthesis is primed using an oligo(dT) primer having a sequencing platform adapter construct (A) at its 5' end, so that the single product nucleic acid has sequencing platform adapter constructs A and B' at its 5' and 3' ends, respectively. The sequencing platform adapter constructs may include less than all of the useful or necessary domains for sequencing on a sequencing platform of interest (e.g., similar to the embodiment shown in FIG. 1) or may include all useful or necessary domains (e.g., similar to the embodiment shown in FIG. 2). Embodiments such as the one shown in FIG. 3 find use, e.g., in generating a sequencing-ready library of cDNAs which correspond to non-polyadenylated RNAs (e.g., microRNAs, small RNAs, siRNAs, or the like) present in a biological sample of interest.

In certain embodiments, the subject methods may be used to generate a cDNA library corresponding to mRNAs for downstream sequencing on a sequencing platform of interest (e.g., a sequencing platform provided by Illumina®, Ion Torrent™, Pacific Biosciences, Life Technologies™, Roche, or the like). In one embodiment, mRNAs are sheared to a length of approximately 200 bp, or any other appropriate length as defined by the sequencing platform being used (e.g. 400-800 bp), and then used as templates in a template switch polymerization reaction as described elsewhere herein. The first strand synthesis is primed using a primer having a sequencing primer binding domain (e.g., an Illumina® Read 2 N6 primer binding domain), and the template switch oligonucleotide includes a second sequencing primer binding domain of the sequencing platform (e.g., an Illumina® Read 1 primer binding domain). In certain aspects, the first strand synthesis is primed using a random primer. The resulting library may then optionally be PCR amplified with primers that add nucleic acid domains that bind to surface-attached sequencing platform oligonucleotides (e.g., the P5 and P7 oligonucleotides attached to the flow cell in an Illumina® sequencing system). The library may be mixed 50:50 with a control library (e.g., Illumina®'s PhiX control library) and sequenced on the sequencing platform (e.g., an Illumina® sequencing system). The control library sequences may be removed and the remaining sequences mapped to the transcriptome of the source of the mRNAs (e.g., human, mouse, or any other mRNA source).

According to certain embodiments, the subject methods may be used to generate a cDNA library corresponding to non-polyadenylated RNAs for downstream sequencing on an Illumina®-based sequencing system. In one embodiment, microRNAs are polyadenylated and then used as templates in a template switch polymerization reaction as described elsewhere herein. The first strand synthesis is primed using an Illumina® dT primer, and the template switch oligonucleotide included an Illumina® Read 1 primer binding domain.

Figure 5:
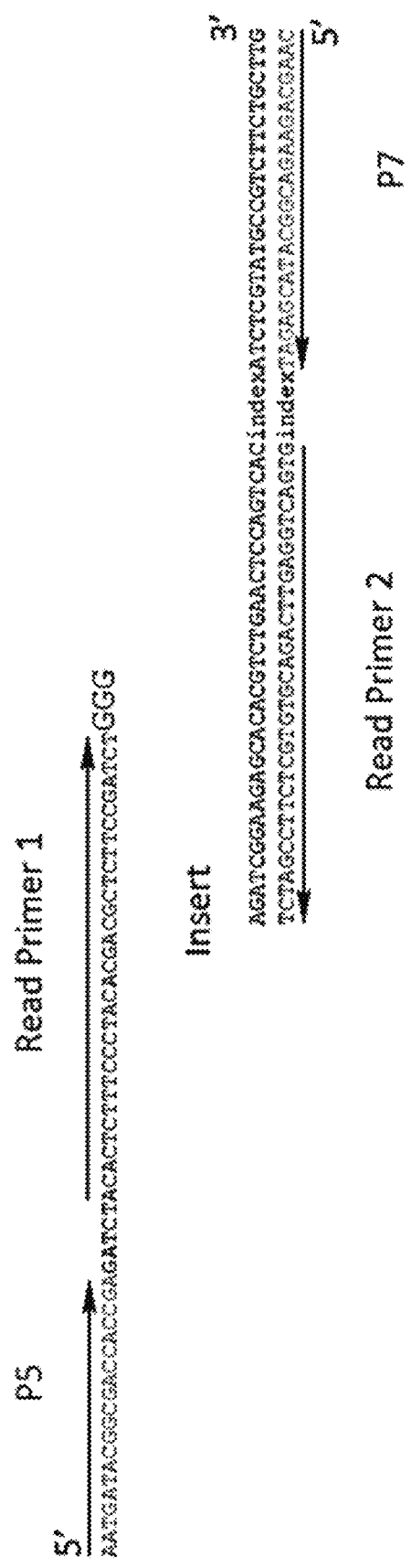
FIG. 5 shows adapter constructs according to one embodiment of the present disclosure. In this embodiment, the constructs include the P5, P7, Read 1, Read 2, and index domains which enable paired-end sequencing of a cDNA corresponding to a template RNA on an Illumina® sequencing platform. From top to bottom, SEQ ID NOs:8-10.
Figure 6:
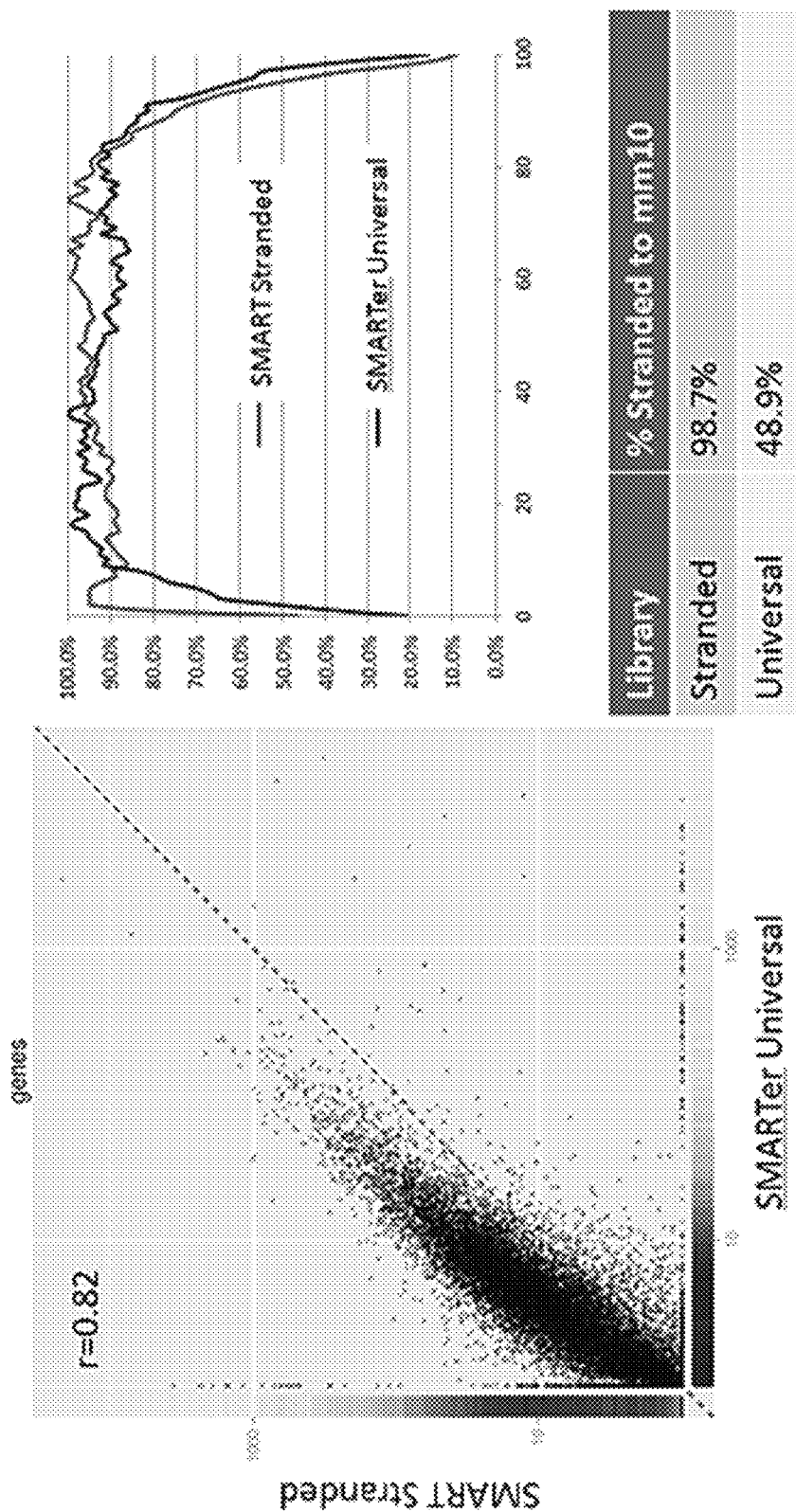
FIG. 6 shows a comparison of sequencing data generated using a method according to one embodiment of the present disclosure and sequencing data generated using the traditional method of separate cDNA amplification and library preparation steps.

FIG. 5 shows example sequences that may be added to nucleic acids according to one embodiment of the present disclosure. In this example, a template switch oligonucleotide (top) includes a 3' hybridization domain (GGG) and a sequencing platform adapter construct that includes a binding site for a surface-attached sequencing platform oligonucleotide (in this example, the surface-attached P5 primer of an Illumina® system) and a sequencing primer binding site (in this example, a binding site for the Read 1 sequencing primer of an Illumina® system) to facilitate sequencing on a sequencing platform of interest. A sequencing platform adapter construct (bottom) which may be included in the nucleic acid at an end opposite the template switch oligonucleotide includes a binding site for a second surface-attached sequencing platform oligonucleotide (in this example, the surface-attached P7 primer of an Illumina® system), an index barcode, and a second sequencing primer binding site (in this example, the binding site for a Read 2 sequencing primer of an Illumina® system) to facilitate sequencing on a sequencing platform of interest.

The subject methods may further include combining a thermostable polymerase (e.g., a Taq, Pfu, Tfl, Tth, Tli, and/or other thermostable polymerase)—in addition to the template switching polymerase—into the reaction mixture. Alternatively, the template switching polymerase may be a thermostable polymerase. Either of these embodiments find use, e.g., when it is desirable to achieve sequencing platform adapter construct addition and amplification (e.g., amplification with or without further adapter addition) of the product nucleic acid in a single tube. For example, the contents of the single tube may be placed under conditions suitable for the template switch polymerization reaction to occur (as described elsewhere herein), followed by placing the reaction contents under thermocycling conditions (e.g., denaturation, primer annealing, and polymerization conditions) in which the first-strand synthesis product is PCR amplified using amplification primers and the thermostable polymerase present in the single tube. Due to its thermostability, the thermostable polymerase will retain its activity even when present during the PCR phase of this embodiment.

Compositions

Also provided by the present disclosure are compositions. The subject compositions may include, e.g., one or more of any of the reaction mixture components described above with respect to the subject methods. For example, the compositions may include one or more of a template ribonucleic acid (RNA), a polymerase (e.g., a polymerase capable of template-switching, a thermostable polymerase, combinations thereof, or the like), a template switch oligonucleotide, dNTPs, a salt, a metal cofactor, one or more nuclease inhibitors (e.g., an RNase inhibitor), one or more enzyme-stabilizing components (e.g., DTT), or any other desired reaction mixture component(s).

In certain aspects, the subject compositions include a template ribonucleic acid (RNA) and a template switch oligonucleotide each hybridized to adjacent regions of a nucleic acid strand, where the template switch oligonucleotide includes a 3' hybridization domain and a sequencing platform adapter construct. The sequencing platform adapter construct may include any sequencing platform nucleic acid domain of interest, including any of the domains described above with respect to the subject methods (e.g., a domain that specifically binds to a surface-attached sequencing platform oligonucleotide, a sequencing primer binding domain, a barcode domain, a barcode sequencing primer binding domain, a molecular identification domain, or any combination thereof). Approaches for isolating RNA samples from a nucleic acid source of interest, as well as strategies for generating template RNAs from precursor RNAs, are described elsewhere herein.

In certain aspects, the 3' hybridization domain of the template switch oligonucleotide includes an arbitrary sequence, e.g., as described above.

The subject compositions may be present in any suitable environment. According to one embodiment, the composition is present in a reaction tube (e.g., a 0.2 mL tube, a 0.6 mL tube, a 1.5 mL tube, or the like) or a well. In certain aspects, the composition is present in two or more (e.g., a plurality of) reaction tubes or wells (e.g., a plate, such as a 96-well plate). The tubes and/or plates may be made of any suitable material, e.g., polypropylene, or the like. In certain aspects, the tubes and/or plates in which the composition is present provide for efficient heat transfer to the composition (e.g., when placed in a heat block, water bath, thermocycler, and/or the like), so that the temperature of the composition may be altered within a short period of time, e.g., as necessary for a particular enzymatic reaction to occur. According to certain embodiments, the composition is present in a thin-walled polypropylene tube, or a plate having thin-walled polypropylene wells. In certain embodiments it may be convenient for the reaction to take place on a solid surface or a bead, in such case, the template switch oligonucleotide or one or more of the primers may be attached to the solid support or bead by methods known in the art—such as biotin linkage or by covalent linkage) and reaction allowed to proceed on the support.

Other suitable environments for the subject compositions include, e.g., a microfluidic chip (e.g., a "lab-on-a-chip device"). The composition may be present in an instrument configured to bring the composition to a desired temperature, e.g., a temperature-controlled water bath, heat block, or the like. The instrument configured to bring the composition to a desired temperature may be configured to bring the composition to a series of different desired temperatures, each for a suitable period of time (e.g., the instrument may be a thermocycler).

Kits

Aspects of the present disclosure also include kits. The kits may include, e.g., one or more of any of the reaction mixture components described above with respect to the subject methods. For example, the kits may include one or more of a template ribonucleic acid (RNA), components for producing a template RNA from a precursor RNA (e.g., a poly(A) polymerase and associated reagents for polyadenylating a non-polyadenylated precursor RNA), a polymerase (e.g., a polymerase capable of template-switching, a thermostable polymerase, combinations thereof, or the like), a template switch oligonucleotide, dNTPs, a salt, a metal cofactor, one or more nuclease inhibitors (e.g., an RNase inhibitor and/or a DNase inhibitor), one or more molecular crowding agents (e.g., polyethylene glycol, or the like), one or more enzyme-stabilizing components (e.g., DTT), or any other desired kit component(s), such as solid supports, e.g., tubes, beads, microfluidic chips, etc.

According to one embodiment, the subject kits include a template switch oligonucleotide comprising a 3' hybridization domain and a sequencing platform adapter construct, and a template switching polymerase. The sequencing platform adapter construct may include any sequencing platform nucleic acid domain of interest, including any of the domains described above with respect to the subject methods and compositions (e.g., a domain that specifically binds to a surface-attached sequencing platform oligonucleotide, a sequencing primer binding domain, a barcode domain, a barcode sequencing primer binding domain, a molecular identification domain, or any combination thereof).

Kits of the present disclosure may include a first-strand synthesis primer that includes a first domain that hybridizes to a template RNA and a second domain that does not hybridize to the template RNA. The first domain may have a defined or arbitrary sequence. The second domain of such primers may include, e.g., a sequencing platform adapter construct that includes a nucleic acid domain selected from a domain that specifically binds to a surface-attached sequencing platform oligonucleotide, a sequencing primer binding domain, a barcode domain, a barcode sequencing primer binding domain, a molecular identification domain, and any combination thereof.

In certain embodiments, the kits include reagents for isolating RNA from a source of RNA. The reagents may be suitable for isolating nucleic acid samples from a variety of RNA sources including single cells, cultured cells, tissues, organs, or organisms. The subject kits may include reagents for isolating a nucleic acid sample from a fixed cell, tissue or organ, e.g., formalin-fixed, paraffin-embedded (FFPE) tissue. Such kits may include one or more deparaffinization agents, one or more agents suitable to de-crosslink nucleic acids, and/or the like.

Components of the kits may be present in separate containers, or multiple components may be present in a single container. For example, the template switch oligonucleotide and the template switching polymerase may be provided in the same tube, or may be provided in different tubes. In certain embodiments, it may be convenient to provide the components in a lyophilized form, so that they are ready to use and can be stored conveniently at room temperature.

In addition to the above-mentioned components, a subject kit may further include instructions for using the components of the kit, e.g., to practice the subject method. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, Hard Disk Drive (HDD) etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Utility

The subject methods find use in a variety of applications, including those that require the presence of particular nucleotide sequences at one or both ends of nucleic acids of interest. Such applications exist in the areas of basic research and diagnostics (e.g., clinical diagnostics) and include, but are not limited to, the generation of sequencing-ready cDNA libraries. Such libraries may include adapter sequences that enable sequencing of the library members using any convenient sequencing platform, including: the HiSeq™, MiSeq™ and Genome Analyzer™ sequencing systems from Illumina®; the Ion PGM™ and Ion Proton™ sequencing systems from Ion Torrent™; the PACBIO RS II sequencing system from Pacific Biosciences, the SOLiD sequencing systems from Life Technologies™, the 454 GS FLX+ and GS Junior sequencing systems from Roche, or any other convenient sequencing platform. The methods of the present disclosure find use in generating sequencing ready cDNA libraries corresponding to any RNA starting material of interest (e.g., mRNA) and are not limited to polyadenylated RNAs. For example, the subject methods may be used to generate sequencing-ready cDNA libraries from non-polyadenylated RNAs, including microRNAs, small RNAs, siRNAs, and/or any other type non-polyadenylated RNAs of interest. The methods also find use in generating strand-specific information, which can be helpful in determining allele-specific expression or in distinguishing overlapping transcripts in the genome.

An aspect of the subject methods is that—utilizing a template RNA—a cDNA species having sequencing platform adapter sequences at one or both of its ends is generated in a single step, e.g., without the added steps associated with traditional ligation-based approaches for generating hybrid nucleic acid molecules for downstream sequencing applications. Such steps include a ligation step (which may require a prior restriction digest), washing steps, and any other necessary steps associated with traditional ligation-based approaches. Accordingly, the methods of the present disclosure are more efficient, cost-effective, and provide more flexibility than the traditional approaches.

The following examples are offered by way of illustration and not by way of limitation.

Experimental

I. Library Construction

1 µg of Human Brain PolyA RNA (Clontech) was fragmented with addition of 5× fragmentation Buffer (200 mM Tris acetate, pH 8.2, 500 mM potassium acetate, and 150 mM magnesium acetate) and heating at 94° C. for 2 min 30 s. Fragmented RNA was purified using a Nucleospin RNA XS spin column (Macharey Nagel).

Fragmented RNA was diluted to either 1 ng/µl of 5 ng/µl in RNase free water. 1 µl of fragmented RNA or water was combined with 1 µl 12 µM first strand primer and 2.5 µl of RNase free water. Samples were heated to 72° C. for 3 minutes and then placed on ice. To these samples were added 2 µl 5× first strand buffer (Clontech), 0.25 µl 100 mM DTT, 0.25 µl recombinant RNase inhibitor (Takara), 10 mM dNTP mix (Clontech), 1 µl 12 µM template switch oligo and 1 µl SMARTScribe RT (Clontech). Samples were incubated at 42° C. for 90 minutes followed by 70° C. for 10 minutes.

Figure 4:
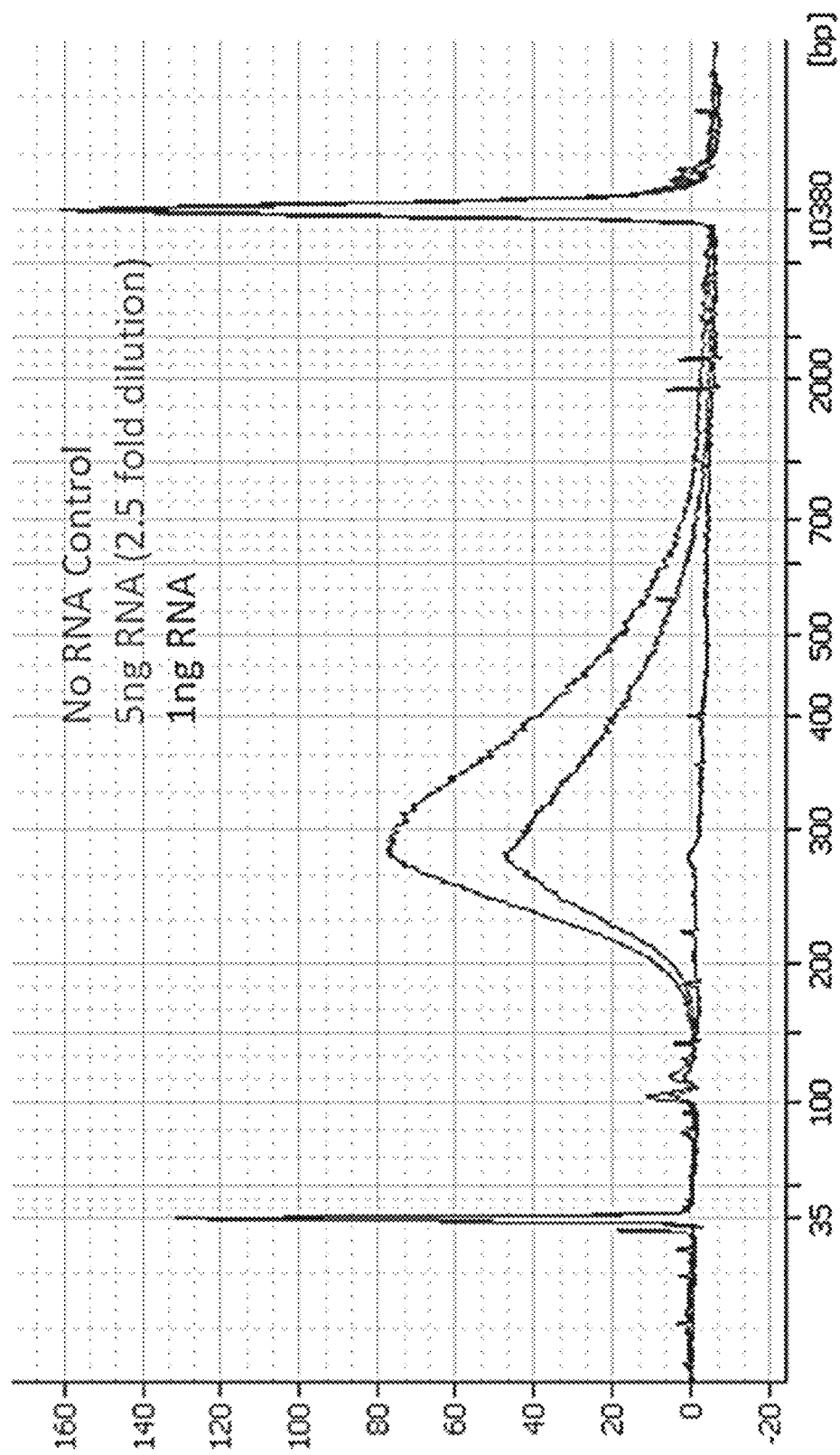
FIG. 4 is a graph showing that a cDNA library may be generated using the methods of the present disclosure with various amounts of input RNA. According to this embodiment, the cDNAs that make up the library have adapter constructs that enable sequencing of the cDNAs by a sequencing platform of interest.

First strand cDNA reactions were purified by addition of 15 µl water and 25 µl Ampure XP beads (Beckman Coulter). Samples were well mixed and incubated at room temperature for 8 minutes. Samples were bound to a magnetic stand for 5 minutes, and the beads were washed twice with 200 µl 80% ethanol and allowed to air dry for 5 minutes.

cDNA on the beads was eluted by addition of 50 µl PCR Mastermix (5 µl 10 Advantage2 buffer, 5 µl GC Melt reagent, 1 µl 10 mM dNTPs, 1 µl Advantage2 polymerase (Clontech), 240 nM forward PCR primer, 240 nM reverse PCR primer, and 36.8 µl water). Samples were thermocycled for 12 PCR cycles with the settings 95° C. 1 minute, 12× (95° C. 15 seconds, 65° C. 30 seconds, 68° C. 1 minute). PCR products were purified with 50 µl Ampure XP beads and eluted in 40 µl TE buffer. Samples were diluted and run on an Agilent Bioanalyzer using the high sensitivity DNA assay. The results are provided in FIG. 4.

II. Construction of Illumina Sequenced Libraries

A. Library Construction

1 µg of Mouse Brain PolyA RNA (Clontech) was fragmented addition of 5× fragmentation Buffer (200 mM Tris acetate, pH 8.2, 500 mM potassium acetate, and 150 mM magnesium acetate) and heating at 94° C. for 2 min 30 s. Fragmented RNA was purified using a Nucleospin RNA XS spin column (Macharey Nagel).

10 ng of fragmented RNA in 3.5 µl was combined with 1 µl 12 µM first strand primer. Samples were heated to 72° C. for 3 minutes and then placed on ice. To these samples were added 2 µl 5× first strand buffer (Clontech), 0.25 µl 100 mM DTT, 0.25 µl recombinant RNase inhibitor (Takara), 10 mM dNTP mix (Clontech), 1 µl 12 µM template switch oligo, and 1 µl SMARTScribe RT (Clontech). Samples were incubated at 42° C. for 90 minutes followed by 70° C. for 10 minutes.

First strand cDNA reactions were purified by addition of 15 µl water and 25 µl Ampure XP beads (Beckman Coulter). Samples were well mixed and incubated at room temperature for 8 minutes. Samples were bound to a magnetic stand for 5 minutes, and the beads were washed twice with 200 µl 80% ethanol and allowed to air dry for 5 minutes.

cDNA on the beads was eluted by addition of 50 µl PCR Mastermix (5 µl 10 Advantage2 buffer, 5 µl GC Melt reagent, 1 µl 10 mM dNTPs, 1 µl Advantage2 polymerase (All Clontech), 240 nM forward PCR primer, 240 nM reverse PCR primer, and 36.8 µl water). Samples were thermocycled for 12 PCR cycles with the settings 95° C. 1 minute, 12× (95° C. 15 seconds, 65° C. 30 seconds, 68° C. 1 minute). PCR products were purified with 50 µl Ampure XP beads and eluted in 40 µl TE buffer. Samples were diluted and run on an Agilent Bioanalyzer using the high sensitivity DNA assay.

B. Sequencing

The above sequencing library was diluted to 2 nM and combined with an equal amount of PhiX Control Library (Illumina). Samples were loaded onto an Illumina MiSeq instrument with a final loading concentration of 8 pM and sequenced as a single 66 bp read.

C. Analysis Summary

All Analysis was performed on a linux workstation. Sequences were trimmed of the first three nucleotides, and PhiX sequences were bioinformatically removed by mapping all sequences to the PhiX genome with the Bowtie2 software package and retaining all unmapped reads.

Remaining sequencing reads were mapped to the mouse transcriptome (build MM10) using the tophat2 software package. Gene expression values were calculated using the Cufflinks software using the genome annotation as a guide.

Gene expression values were compared to a previously sequenced library generated with the SMARTer Universal kit (Clontech) from ribosomally depleted Mouse Brain Total RNA (Clontech).

Gene expression comparisons and plotting were done In R using the CummeRbund analysis package.

Gene body coverage and strand specificity were calculated using geneBody_coverage.py and infer_experiment.py scripts respectively from the RSeQC software collection.

III. miRNA Library Construction

1 µl of 5 µM synthetic miR-22 (AAGCUGCCA-GUUGAAGAACUGUA) (RNA) (SEQ ID NO:07) was combined with 2 µl 5X First Strand Buffer (Clontech), 0.25 µl 100 mM DTT, 0.25 µl Recombinant RNase inhibitor (Takara), 0.25 µl Poly(A) polymerase (Takara), 1 µl 10 mM ATP, 5.25 µl RNase free water. Samples were incubated at 37° C. for 10 minutes followed by 65° C. for 20 minutes.

Reactions were diluted with 10 µl RNase free water. 3.5 µl diluted polyadenylated miRNA was combined with 1 µl 12 µM first strand primer. Samples were heated to 72° C. for 3 minutes and then placed on ice. To these samples were added 2 µl 5× first strand buffer (Clontech), 0.25 µl 100 mM DTT, 0.25 µl recombinant RNase inhibitor (Takara), 10 mM dNTP mix (Clontech), 1 µl 12 µM template switch oligo, and 1 µl SMARTScribe RT (Clontech). Samples were incubated at 42° C. for 60 minutes followed by 70° C. for 15 minutes.

First strand reactions were diluted with 40 µl TE buffer. 5 µl diluted cDNA was combined with 45 µl PCR Mastermix (5 µl 10 Advantage2 buffer, 1 µl 10 mM dNTPs, 1 µl Advantage2 polymerase (All Clontech), 240 nM forward PCR primer, 240 nM reverse PCR primer (and 36 µl water). Samples were thermocycled for 20 PCR cycles with the settings 95° C. 1 minute, 20× (95° C. 15 seconds, 65° C. 30 seconds). 5 µl PCR products were resolved on a 1% agarose gel.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method comprising:
   a) combining:
   i) a RNA sample isolated from 9 cells or less than 9 cells and comprising a template ribonucleic acid (RNA);
   ii) a template switch oligonucleotide comprising a first nucleotide sequence domain;
   iii) a polymerase having terminal transferase activity;
   iv) a first strand primer comprising a first domain that hybridizes to the template RNA wherein the first strand primer includes a second domain having a nucleotide sequence that is different from said first nucleotide sequence domain present in the template switch oligonucleotide; and
   v) dNTPs;
     in a reaction mixture under conditions such that producing a product nucleic acid comprising the template RNA and the template switch oligonucleotide which are hybridized to adjacent regions of a single product nucleic acid comprising the first strand primer and a region polymerized from the dNTPs by the polymerase;
   b) amplifying the product nucleic acid with a forward primer and a reverse primer, wherein each of the forward primer and the reverse primer comprises a sequencing platform adapter construct comprising at least a portion of a capture sequence that is utilized by a sequencing platform, wherein the capture sequence specifically hybridizes to a surface-attached sequencing platform oligonucleotide on the sequencing platform, and wherein the forward and reverse primers are different and hybridize to different sequences of the product nucleic acid; and
   c) sequencing an amplified product nucleic acid produced in step (b) by the sequencing platform that comprises the surface-attached sequencing platform oligonucleotide that captures the at least portion of the capture sequence of the sequencing platform adapter construct; wherein the sequencing platform is a next generation sequencing platform and the sequencing platform adaptor construct comprises the sequence selected from the group consisting of SEQ ID NOs: 01 to 06, which are P5 domain, P7 domain, Read 1 primer domain, Read 2 primer domain, A adapter domain and P1 adapter domain.

2. The method according to claim 1, wherein the less than 9 cells are 5 cells or less than 5 cells.

3. The method according to claim 2, wherein the less than 5 cells is a single cell.

4. The method according to claim 1, wherein the template RNA is a messenger RNA (mRNA).

5. The method according to claim 1, wherein the template RNA is a non-polyadenylated RNA.

6. The method according to claim 5, wherein the method, prior to the combining step (a), further comprises adding a nucleic acid sequence to the 3' end of the non-polyadenylated RNA.

7. The method according to claim 6, wherein the nucleic acid sequence added to the 3' end of the non-polyadenylated RNA is a polyadenine sequence.

8. The method according to claim 5, wherein the non-polyadenylated RNA is a microRNA (miRNA).

9. The method according to claim 1, wherein the template RNA is a polyadenylated RNA having a polyadenylation sequence.

10. The method according to claim 1, wherein the polymerase is a reverse transcriptase.

11. The method according to claim 1, wherein the first strand primer comprises a modification that prevents a polymerase using the single product nucleic acid as a template from polymerizing a nascent strand beyond the modification in the first strand primer.

12. The method according to claim 1, wherein the template switch oligonucleotide comprises a modification that prevents the polymerase from switching from the template switch oligonucleotide to a different template nucleic acid after synthesizing the complement of said first nucleotide sequence domain present in the template switch oligonucleotide.

13. The method according to claim 12, wherein the modification is selected from the group consisting of: an abasic lesion, a nucleotide adduct, an iso-nucleotide base, and combinations thereof.

14. The method according to claim 1, wherein the template switch oligonucleotide comprises one or more nucleotide analogs.

15. The method according to claim 1, wherein the template switch oligonucleotide comprises a linkage modification, an end modification, or both the linkage modification and the end modification.

16. The method according to claim 1, wherein the template switch oligonucleotide, the first strand primer, or both the template switch oligonucleotide and the first strand primer comprise a sequencing platform adapter construct that is utilized by a sequencing platform.

17. The method according to claim 16, wherein the sequencing platform adapter construct comprises a nucleic acid domain selected from the group consisting of: a domain that specifically hybridizes to the surface-attached sequencing platform oligonucleotide, a sequencing primer binding domain, a barcode domain, a barcode sequencing primer binding domain, a molecular identification domain, and combinations thereof.

18. The method according to claim 16, wherein the sequencing platform adapter construct further comprises a portion of a nucleic acid domain utilized by a sequencing platform.

19. The method according to claim 16, wherein the sequencing platform adapter construct further comprises a complete nucleic acid domain utilized by a sequencing platform.

20. The method according to claim 1, wherein the forward primer and the reverse primer comprise different sequencing platform adapter constructs.

21. The method according to claim 1, wherein the method does not include a ligation step.

22. The method according to claim 1, wherein each of said first nucleotide sequence domain of the template switch oligonucleotide and said second domain of the first strand primer comprises a sequencing platform adapter construct that is utilized by a sequencing platform.

23. The method according to claim 1, wherein the amplified product nucleic acid produced in step (b) comprises the sequencing platform adapter construct at its both ends and said sequencing the amplified product nucleic acid in step (c) comprises sequencing the amplified product nucleic acid from its both ends using the sequencing platform adapter construct and the surface-attached sequencing platform oligonucleotide.

24. The method according to claim 1, wherein the capture sequence is from 6 to 75 nucleotides in length and the sequencing platform adapter construct specifically hybridizes to the surface-attached sequencing platform oligonucleotide utilized by a sequencing platform.

25. A method comprising: a) combining:
i) a RNA sample isolated from 9 cells or less than 9 cells and comprising a template ribonucleic acid (RNA);
ii) a template switch oligonucleotide comprising a first nucleotide sequence domain;
iii) a polymerase having terminal transferase activity;
iv) a first strand primer comprising a first domain that hybridizes to the template RNA wherein the first strand primer includes a second domain having a nucleotide sequence that is different from said first nucleotide sequence domain present in the template switch oligonucleotide; and
v) dNTPs;
in a reaction mixture under conditions such that producing a product nucleic acid comprising the template RNA and the template switch oligonucleotide which are hybridized to adjacent regions of a single product nucleic acid comprising the first strand primer and a region polymerized from the dNTPs by the polymerase;
b) amplifying the product nucleic acid with a forward primer and a reverse primer, wherein the forward primer comprises a first sequencing platform adapter construct and the reverse primer comprises a second sequencing platform adapter construct, thereby generating an amplified product nucleic acid with the first sequencing platform adapter construct at its one end and the second sequencing platform adapter construct at its other end, wherein the first sequencing platform adapter construct comprises a capture sequence from 16 to 22 nucleotides in length specifically hybridized to SEQ ID NO: 01 or SEQ ID No:02, which is a surface-attached P5 or P7 sequencing platform oligonucleotide utilized by a sequencing platform and the second sequencing platform adapter construct comprises at least a portion of a capture sequence that is from 6 to 75 nucleotides in length and specifically hybridizes to a surface-attached sequencing platform oligonucleotide utilized by the sequencing platform, and wherein the forward and reverse primers are different and hybridize to different sequences of the product nucleic acid; and
c) sequencing the amplified product nucleic acid on the sequencing platform using both the first sequencing platform adapter construct and the second sequencing platform adapter construct and the surface-attached P5 or P7 sequencing platform oligonucleotide.

* * * * *

```
                      SEQUENCE LISTING

<160> NUMBER OF SEQ ID NOS: 12

<210> SEQ ID NO 1
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1
aatgatacgg cgaccaccga                                                  20

<210> SEQ ID NO 2
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 2
caagcagaag acggcatacg agat                                             24

<210> SEQ ID NO 3
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 3
acactctttc cctacacgac gctcttccga tct                                   33

<210> SEQ ID NO 4
<211> LENGTH: 34
<212> TYPE: DNA
<213> ORGANISM: Artificial sequence
<220> FEATURE:
<223> OTHER INFORMATION: Synthetic oligonucleotide

<400> SEQUENCE: 4
gtgactggag ttcagacgtg tgctcttccg atct                                  34

<210> SEQ ID NO 5
```

```
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 5
ccatctcatc cctgcgtgtc tccgactcag                                        30

<210> SEQ ID NO 6
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 6
cctctctatg ggcagtcggt gat                                               23

<210> SEQ ID NO 7
<211> LENGTH: 23
<212> TYPE: RNA
<213> ORGANISM: Artificial sequence
<220> FEATURE:
<223> OTHER INFORMATION: Synthetic oligonucleotide

<400> SEQUENCE: 7
aagcugccag uugaagaacu gua                                               23

<210> SEQ ID NO 8
<211> LENGTH: 61
<212> TYPE: DNA
<213> ORGANISM: Artificial sequence
<220> FEATURE:
<223> OTHER INFORMATION: Synthetic oligonucleotide

<400> SEQUENCE: 8
aatgatacgg cgaccaccga gatctacact ctttccctac acgacgctct tccgatctgg       60
g                                                                       61

<210> SEQ ID NO 9
<211> LENGTH: 258
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (35)..(234)
<223> OTHER INFORMATION: n at positions 35-234 may be any nucleotide and
      between 4 and 200 of the nucleotides may be present.

<400> SEQUENCE: 9
agatcggaag agcacacgtc tgaactccag tcacnnnnnn nnnnnnnnnn nnnnnnnnnn       60
nnnnnnnnnn nnnnnnnnnn nnnnnnnnnn nnnnnnnnnn nnnnnnnnnn nnnnnnnnnn      120
nnnnnnnnnn nnnnnnnnnn nnnnnnnnnn nnnnnnnnnn nnnnnnnnnn nnnnnnnnnn      180
nnnnnnnnnn nnnnnnnnnn nnnnnnnnnn nnnnnnnnnn nnnnnnnnnn nnnnatctcg      240
tatgccgtct tctgcttg                                                    258

<210> SEQ ID NO 10
<211> LENGTH: 258
<212> TYPE: DNA
<213> ORGANISM: Artificial sequence
<220> FEATURE:
```

```
<223> OTHER INFORMATION: Synthetic oligonucleotide
<220> FEATURE:
<221> NAME/KEY: misc_feature
<222> LOCATION: (25)..(224)
<223> OTHER INFORMATION: n at positions 25-224 may be any nucleotide and
      between 4 and 200 of the nucleotides may be present.

<400> SEQUENCE: 10
caagcagaag acggcatacg agatnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnngtgact ggagttcaga     240
cgtgtgctct tccgatct                                                   258

<210> SEQ ID NO 11
<211> LENGTH: 14
<212> TYPE: DNA
<213> ORGANISM: Artificial Sequence
<220> FEATURE:
<223> OTHER INFORMATION: poly-adenosine sequence
<220> FEATURE:
<221> NAME/KEY: misc_feature
<222> LOCATION: (14)..(14)
<223> OTHER INFORMATION: the nucleotide at this position may be repeated
      n times

<400> SEQUENCE: 11
aaaaaaaaaa aaaa                                                        14

<210> SEQ ID NO 12
<211> LENGTH: 13
<212> TYPE: DNA
<213> ORGANISM: Artificial Sequence
<220> FEATURE:
<223> OTHER INFORMATION: poly-thymidine sequence

<400> SEQUENCE: 12
tttttttttt ttt                                                         13
```